(12) United States Patent
Tsai

(10) Patent No.: US 11,278,674 B2
(45) Date of Patent: Mar. 22, 2022

(54) SEALED MEDICATION DISPENSING AND ADMINISTERING DEVICE

(71) Applicant: Advcare Medical, Inc., Apia (WS)

(72) Inventor: Hsi Chin Tsai, New Taipei (TW)

(73) Assignee: Advcare Medical, Inc., Apia (WS)

( * ) Notice: Subject to any disclaimer, the term of this patent is extended or adjusted under 35 U.S.C. 154(b) by 316 days.

(21) Appl. No.: 16/500,506

(22) PCT Filed: May 19, 2017

(86) PCT No.: PCT/CN2017/084998
§ 371 (c)(1),
(2) Date: Oct. 3, 2019

(87) PCT Pub. No.: WO2018/209668
PCT Pub. Date: Nov. 22, 2018

(65) Prior Publication Data
US 2020/0069880 A1   Mar. 5, 2020

(51) Int. Cl.
*A61M 1/00* (2006.01)
*A61M 5/31* (2006.01)
(Continued)

(52) U.S. Cl.
CPC .......... *A61M 5/3146* (2013.01); *A61J 1/1406* (2013.01); *A61J 1/201* (2015.05);
(Continued)

(58) Field of Classification Search
CPC ........ A61M 5/3146; A61M 2005/3114; A61M 2005/3123; A61M 2005/3128;
(Continued)

(56) References Cited

U.S. PATENT DOCUMENTS 3,749,084 A * 7/1973 Cucchiara .......... A61B 5/02755
600/575
5,401,245 A   3/1995 Haining
(Continued)

FOREIGN PATENT DOCUMENTS

CN   102614557 A   8/2012
CN   203609751 U   5/2014
(Continued)

*Primary Examiner* — Rebecca E Eisenberg
(74) *Attorney, Agent, or Firm* — Alan D. Kamrath; Karin L. Williams; Mayer & Williams PC

(57) ABSTRACT

A sealed medication dispensing and administering device has a syringe, a plunger, a connecting holder, an elastic valve, and a liquid stopper. The syringe has an outer barrel having an air inlet tube and an inner barrel inserted inside the outer barrel and having a medication inlet tube. The plunger is inserted within the outer and inner barrels. The connecting holder is connected to the syringe and has a connecting cover with at least one outer connecting hole and two piercing needles respectively piercing inside the air inlet tube and the medication inlet tube. Inner spaces of the two piercing needles communicate with the at least one outer connecting hole. The elastic valve selectively covers the two piercing needles. The fluid stopper is disposed within the connecting cover and blocks one of the at least one outer connecting hole and the inner space of the air inlet tube.

15 Claims, 27 Drawing Sheets

(51) Int. Cl.
  *A61J 1/20* (2006.01)
  *A61J 1/14* (2006.01)
  *A61M 5/162* (2006.01)
  *A61M 5/19* (2006.01)
  *A61M 5/315* (2006.01)
  *A61M 5/32* (2006.01)
  *A61M 5/38* (2006.01)

(52) U.S. Cl.
  CPC ........... *A61J 1/2037* (2015.05); *A61J 1/2058* (2015.05); *A61J 1/2072* (2015.05); *A61J 1/2082* (2015.05); *A61J 1/2096* (2013.01); *A61M 5/162* (2013.01); *A61M 5/19* (2013.01); *A61M 5/3134* (2013.01); *A61M 5/3145* (2013.01); *A61M 5/31513* (2013.01); *A61M 5/3294* (2013.01); *A61M 5/385* (2013.01); *A61M 2005/1623* (2013.01); *A61M 2005/3107* (2013.01); *A61M 2005/3114* (2013.01); *A61M 2005/3123* (2013.01); *A61M 2005/3128* (2013.01); *A61M 2005/3131* (2013.01)

(58) Field of Classification Search
  CPC .... A61M 2005/3131; A61M 2039/266; A61M 5/162; A61M 5/1782; A61M 5/19; A61J 1/1406; A61J 1/2037; A61J 1/2072; A61J 1/2096
  See application file for complete search history.

(56) References Cited

U.S. PATENT DOCUMENTS

| | | | |
|---|---|---|---|
| 6,994,315 B2 | 2/2006 | Ryan et al. | |
| 10,064,998 B2 | 9/2018 | Duinat et al. | |
| 11,083,670 B2* | 8/2021 | Ivosevic | A61J 1/2096 |
| 2002/0193777 A1* | 12/2002 | Aneas | A61J 1/2096 |
| | | | 604/411 |
| 2003/0120221 A1 | 6/2003 | Vaillancourt | |
| 2005/0151105 A1 | 7/2005 | Ryan et al. | |
| 2010/0084041 A1 | 4/2010 | Fehr et al. | |
| 2011/0106021 A1* | 5/2011 | Ruegg | A61Q 19/08 |
| | | | 604/290 |
| 2012/0197232 A1* | 8/2012 | Lee | A61M 5/19 |
| | | | 604/506 |
| 2013/0046252 A1 | 2/2013 | Yavorsky et al. | |
| 2014/0261876 A1* | 9/2014 | Mansour | A61J 1/20 |
| | | | 141/27 |
| 2015/0209502 A1* | 7/2015 | Bare | A61B 5/150251 |
| | | | 604/506 |
| 2015/0250680 A1* | 9/2015 | Browka | A61J 1/201 |
| | | | 604/506 |
| 2015/0359709 A1* | 12/2015 | Kriheli | A61J 1/201 |
| | | | 604/405 |
| 2015/0374929 A1* | 12/2015 | Hyde | A61M 5/422 |
| | | | 604/191 |
| 2016/0256632 A1* | 9/2016 | Fangrow | A61J 1/2058 |
| 2017/0007771 A1 | 1/2017 | Duinat et al. | |
| 2017/0014618 A1* | 1/2017 | Ueda | A61M 39/1011 |
| 2017/0360342 A1* | 12/2017 | Hopkins | A61B 5/154 |
| 2018/0161245 A1* | 6/2018 | Kriheli | A61J 1/2065 |
| 2018/0177955 A1 | 6/2018 | Aneas | |
| 2018/0304017 A1 | 10/2018 | Edwards et al. | |
| 2019/0117514 A1* | 4/2019 | Denenburg | A61M 5/162 |
| 2019/0193921 A1* | 6/2019 | Kolonia | B05C 17/00593 |
| 2019/0282797 A1* | 9/2019 | Tsai | A61J 1/2037 |
| 2019/0366004 A1* | 12/2019 | Ma | A61M 5/3135 |
| 2020/0276388 A1* | 9/2020 | Schabbach | A61J 1/1406 |
| 2020/0397991 A1* | 12/2020 | Wickersham | A61M 5/3291 |
| 2021/0093785 A1* | 4/2021 | Helmer | A61M 5/315 |
| 2021/0330554 A1* | 10/2021 | Ivosevic | A61J 1/2096 |

FOREIGN PATENT DOCUMENTS

| | | |
|---|---|---|
| JP | 3303289 B2 | 7/2002 |
| JP | 2007517631 A | 7/2007 |
| TW | M433206 U | 7/2012 |
| TW | M488998 U | 11/2014 |
| WO | WO2015044834 A1 | 4/2015 |
| WO | WO2016042544 A1 | 3/2016 |

* cited by examiner

SEALED MEDICATION DISPENSING AND ADMINISTERING DEVICE

BACKGROUND OF THE INVENTION

1. Field of the Invention

The present invention relates to a medication dispensing and administering system, and more particularly to a sealed medication dispensing and administering device that can prevent leakage of gas generated by the medication.

2. Description of Related Art

A conventional way for withdrawing and administering medicine is to insert a syringe having a steel needle into a phial containing medicine, withdraw the medicine from the phial and into the syringe, pull out the syringe from the phial, and then inject the medicine into the patient either via a drainage bag, diluent, or direct intravenous injection into a patient.

The conventional way of withdrawing medicine by a syringe does not have additional mechanism for tight sealing and leakage prevention, and therefore, the medicine fluid and the gas volatilized from the medicine are prone to leakage during the processes of medicine withdrawal and injection. A medical institution is an environment exposed to complexity in medication application, which may endanger healthy clinical staffs, and in addition, accidentally leaked medicines could mix with one another, such mixture making the medical institution an extremely risky working environment.

In addition, the clinical staffs could be accidentally injured by needle sticks when processing injection by syringe, and the medicine residues on the needle may cause unnecessary infection to the clinical staffs. Therefore, the conventional way to withdraw and administrate medicine by syringe needles has to be improved.

SUMMARY OF THE INVENTION

A sealed medication dispensing and administering device of the present invention comprises a syringe and a connecting holder. The syringe comprises an outer barrel, an inner barrel, and a plunger. The inner barrel is movably provided inside the outer barrel. The plunger is movably provided inside the inner barrel. The outer barrel comprises an air inlet tube. The inner barrel comprises a medication inlet tube. The connecting holder comprises a connecting cover, two piercing needles, an elastic valve, and a fluid stopper. The two piercing needles are covered by and disposed within the elastic valve. The elastic valve is provided inside connecting cover. The fluid stopper is provided inside one of the piercing needles. Upon connecting of the syringe onto the connecting holder, the air inlet tube and the medication inlet tube press the elastic valve such that the two piercing needles pass through the elastic valve and respectively enter the medication inlet tube and the air inlet tube. The two piercing needles are installed in the connecting holder, and the whole process of medication dispensing and administering is completed inside the connecting holder, thus making the process safe and quick.

DETAILED DESCRIPTION OF PREFERRED EMBODIMENTS

Technical means for achieving estimated purposes are further illustrated as below, accompanied with drawings and embodiments of the present invention.

Figure 1:
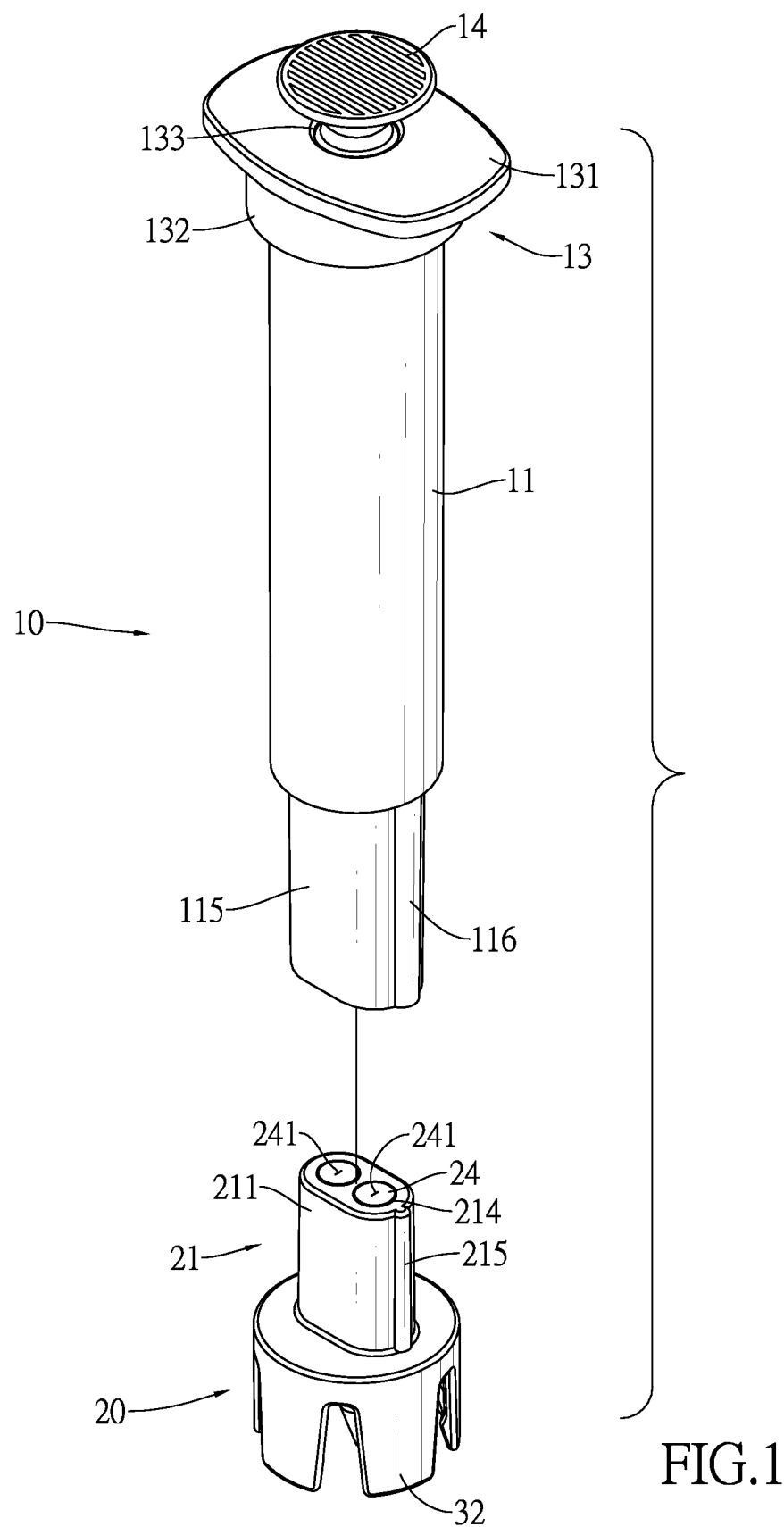
FIG. 1 is a perspective view of a first embodiment of the present invention.

With reference to FIG. 1 a sealed medication dispensing and administering device of a first embodiment in accordance with the present invention has a syringe 10 and a connecting holder 20.

Figure 2:
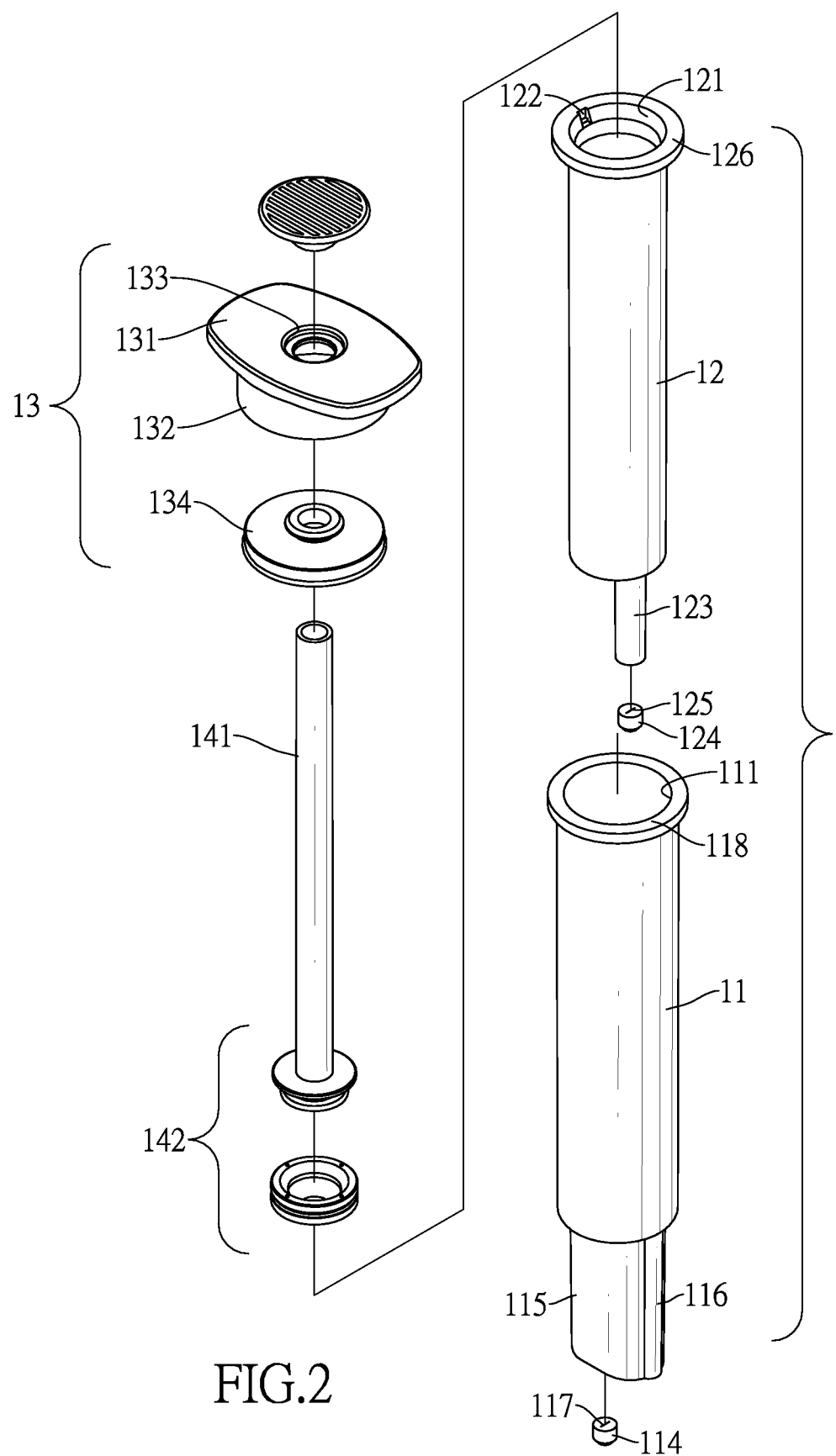
FIG. 2 is an exploded perspective view of a syringe of the present invention.

With reference to FIGS. 1 and 2, the syringe 10 has an outer barrel 11, an inner barrel 12, an airtight cap 13, and a plunger 14.

The outer barrel 11 is a tubular structure with an outer barrel opening 111 defined through a top face of the outer barrel 11. The outer barrel opening 111 has an outer annular rim 118. The outer annular rim 118 horizontally and annularly protrudes from an edge of the outer barrel opening 111.

Figure 4:
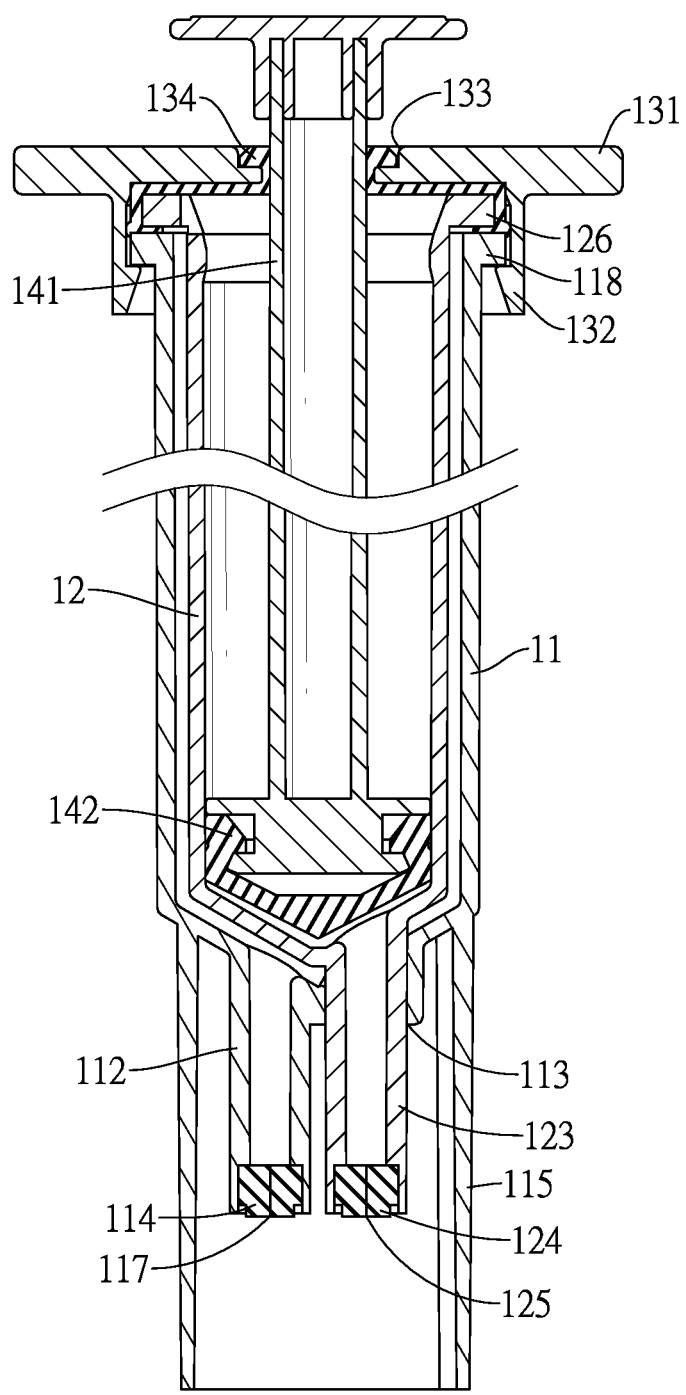
FIG. 4 is a front view in partial section of the syringe of the present invention.

With reference to FIGS. 2 and 4, the outer barrel 11 further has an air inlet tube 112, a connecting hole 113, a rubber stopper 114, an outer cover 115, a fool-proof groove 116, and a first connecting member 119.

The air inlet tube 112 downwardly extends from a lower face of the outer barrel 11. The connecting hole 113 is defined through the lower face of the outer barrel 11 and is spaced from the air inlet tube 112. The rubber stopper 114 is disposed within the air inlet tube 112, and more specifically, the rubber stopper 114 is disposed within the air inlet tube 112 at a position adjacent to an opening that is at a bottom end of the air inlet tube 112. The rubber stopper 114 has a slit 117 that is normally closed, and the rubber stopper 114 normally closes the bottom end of the air inlet tube 112.

In the first embodiment of the present invention, the rubber stopper 114 selectively closes the air inlet tube 112. Materials for manufacturing the stoppers are not restricted, and the stoppers may be made of any materials other than rubber. In the first embodiment, the rubber stopper 114 is fused to be fixed to the bottom end of the air inlet tube 112. Means for fixing the rubber stopper 114 are not limited to the above, and the rubber stopper 114 may be fixed to the bottom end of the air inlet tube 112 by other means.

With reference to FIGS. 1, 2, 4, and 16, the outer cover 115 is annularly formed on an edge of a lower end of the outer barrel 11 and perpendicularly and downwardly extends to enclose the air inlet tube 112 and the connecting hole 113 within the outer cover 115. In the first embodiment, the outer cover 115 is made of materials with flexibility and is partially deformed when subjected to exterior forces. The fool-proof groove 116 is formed in an inner surface of the outer cover 115 such that an outer surface of the outer cover 115 protrudes accordingly. In the first embodiment, the amount of the fool-proof groove 116 is one, and the fool-proof groove 116 is laterally formed in an inner surface of the outer cover 115. The amount and position of the fool-proof groove 116 are not limited to the above. The first connecting unit 119 is disposed on the outer cover 115.

With reference to FIGS. 2 and 4, the inner barrel 12 is inserted inside the outer barrel 11. The inner barrel 12 is downward inserted inside the outer barrel 11 via the outer barrel opening 111. The inner barrel 12 also has an inner barrel opening 121. The inner barrel opening 121 is defined through a top face of the inner barrel 12. The inner barrel opening 121 further has an inner annular rim 126. The inner annular rim 126 horizontally and annularly protrudes from an edge of the inner barrel opening 121. A bottom face of the inner annular rim 126 abuts against a top face of the outer annular rim 118 of the outer barrel 11.

The inner barrel 12 further has a vent 122, a medication inlet tube 123, and a rubber stopper 124. The vent 122 is defined through an inner surface of the inner barrel 12. More specifically, the vent 122 is disposed at a top end of the inner barrel 12 and is adjacent to the inner barrel opening 121. The vent 122 facilitates an inner space of the inner barrel 12 to communicate with an inner space of the outer barrel 11. The medication inlet tube 123 is disposed at a lower face of the inner barrel 12 and is mounted through the connecting hole 113 of the outer barrel 11. The rubber stopper 124 is disposed within the medication inlet tube 123 and at a positon adjacent to an opening that is at a bottom end of the medication inlet tube 123. The rubber stopper 124 has a slit 125 that is normally closed, and the rubber stopper 124 normally closes the bottom end of the medication inlet tube 123.

In the first embodiment, the rubber stopper 124 selectively closes the medication inlet tube 123. Materials for manufacturing the stoppers 124 are not limited to the above, and the stoppers 124 may be made by any materials other than rubber. In the first embodiment, the rubber stopper 124 is fused to be fixed to the bottom end of the medication inlet tube 123. Means for fixing the rubber stopper 124 are not limited to the above, and the rubber stopper 124 may be fixed to the bottom end of the medication inlet tube 123 by other means.

With reference to FIGS. 1 and 4, the airtight cap 13 is disposed on the top faces of the outer barrel 11 and the inner barrel 12, and covers the outer barrel opening 111 and the inner barrel opening 121. The airtight cap 13 has a top cover 131, an engaging portion 132, a central opening 133, and an airtight ring 134. The top cover 131 is disposed above the inner barrel opening 121 and covers the inner barrel opening 121 and the outer barrel opening 111. The engaging portion 132 is an annular wall, and downwardly extends from a bottom face of the top cover 131. When the airtight cover 13 is assembled to the syringe 10, the engaging portion 132 downwardly extends to a bottom face of the outer annular rim 118 and pushes the bottom face of the outer annular rim 118 upward to make the outer annular rim 118 tightly abut against the inner annular rim 126. The engaging portion 132 makes the outer barrel 11 and the inner barrel 12 clamped and fixed to each other via a clamping mechanism mentioned above.

The central opening 133 is defined through a center of the top cover 131. The central opening 133 communicates with an inner space of the inner barrel 12.

With reference to FIG. 4, the airtight ring 134 is disposed between and tightly abuts against a bottom face of the airtight cap 13 and the top face of the inner barrel 12. More specifically, in the first embodiment, the airtight ring 134 is disposed on the bottom face of the top cover 131 and an inner surface of the engaging portion 132. The airtight ring 134 is utilized to fulfill a gap between the inner annular rim 126 and the top cover 131. In addition, a central segment of the airtight ring 134 upward extends and annularly and tightly abuts an inner surface of the central opening 133. In the first embodiment, the arrangement of the airtight ring 134 makes the airtight cap 13 capable of more tightly sealing and clamping the outer barrel 11 and the inner barrel 12.

With reference to FIGS. 1, 2, and 4, the plunger 14 is up-and-down moveably inserted through the outer barrel 11 and the inner barrel 12. The plunger 14 further includes a rod portion 141 and a piston 142. The rod portion 141 is downward inserted into the inner space of the inner barrel 12 via the central opening 133 of the airtight cap 13. The piston 142 is disposed at a bottom end of the rod portion 141 and is disposed in the inner space of the inner barrel 12. The piston 142 longitudinally divides the inner space of the inner barrel 12 into two parts that are free from communicating with each other. Wherein, an upper part of the inner space of the inner barrel 12 communicates with the vent 122.

Figure 3:
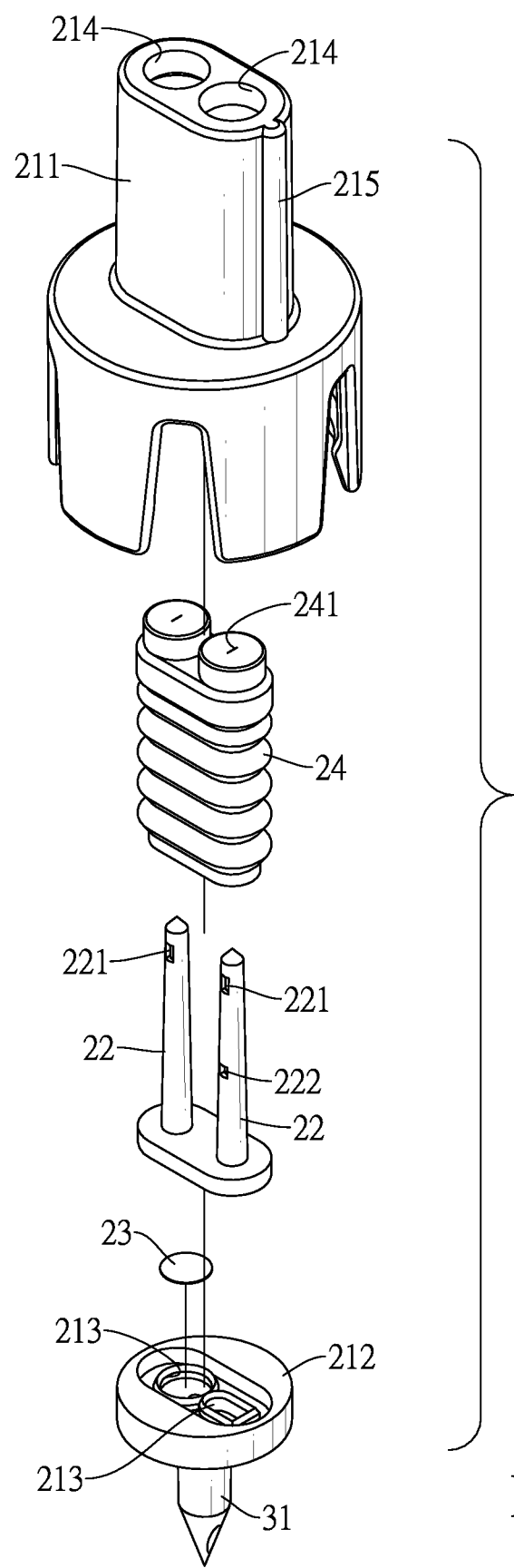
FIG. 3 is an exploded perspective view of a connecting holder of the first embodiment of the present invention.
Figure 25:
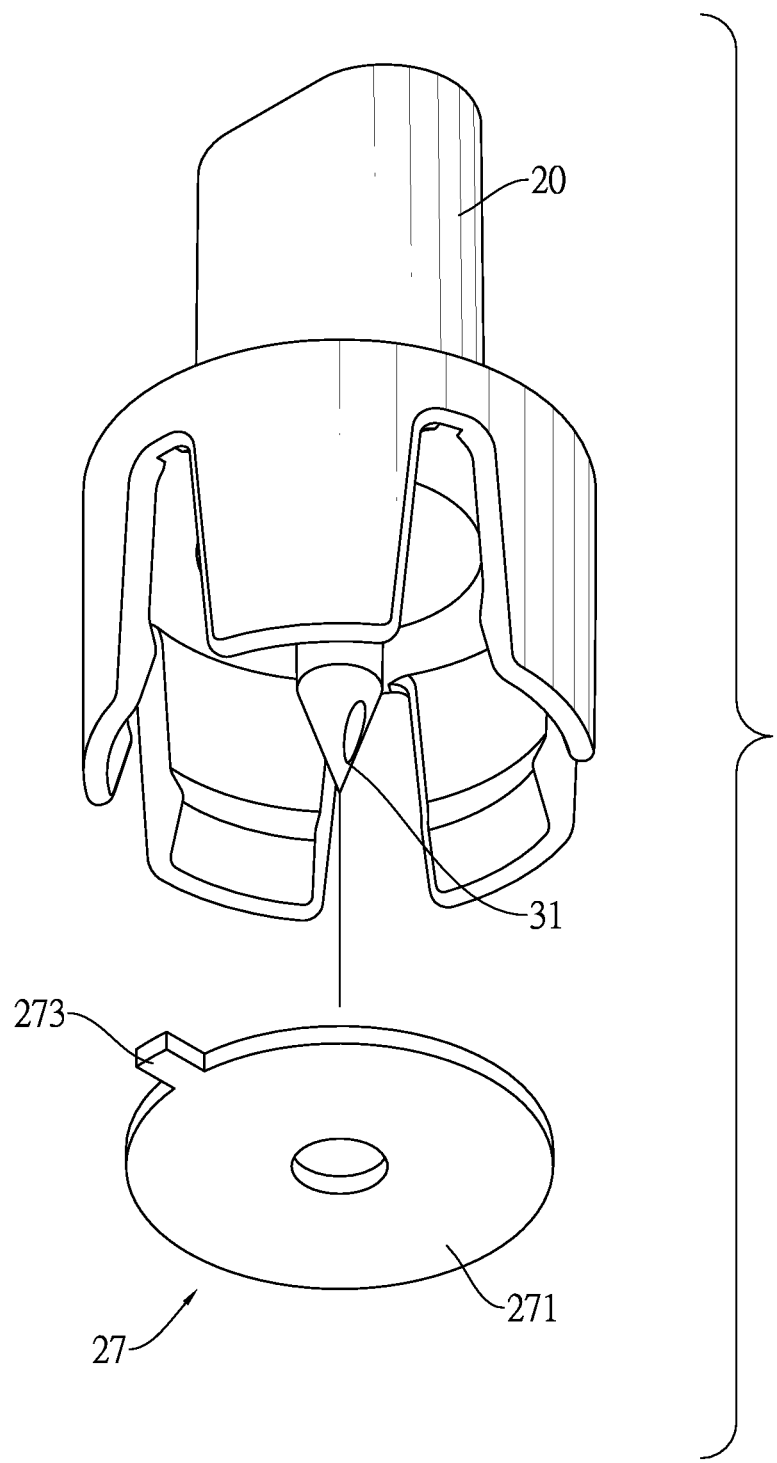
FIG. 25 is an exploded perspective view of the connecting holder and a leakage-proof unit of the present invention.

With reference to FIGS. 1, 3, and 25, the connecting holder 20 is detachably connected to the syringe 10. The connecting holder 20 has a connecting cover 21, two piercing needles 22, a fluid stopper 23, an elastic valve 24, a second connecting unit 25, and a leak-proof unit 27.

The connecting cover 21 corresponds to the outer over 115 in shape. In other words, when the syringe 10 is mounted on and around the connecting holder 20, an outer surface of the connecting cover 21 abuts the inner surface of the outer cover 115.

Figure 5:
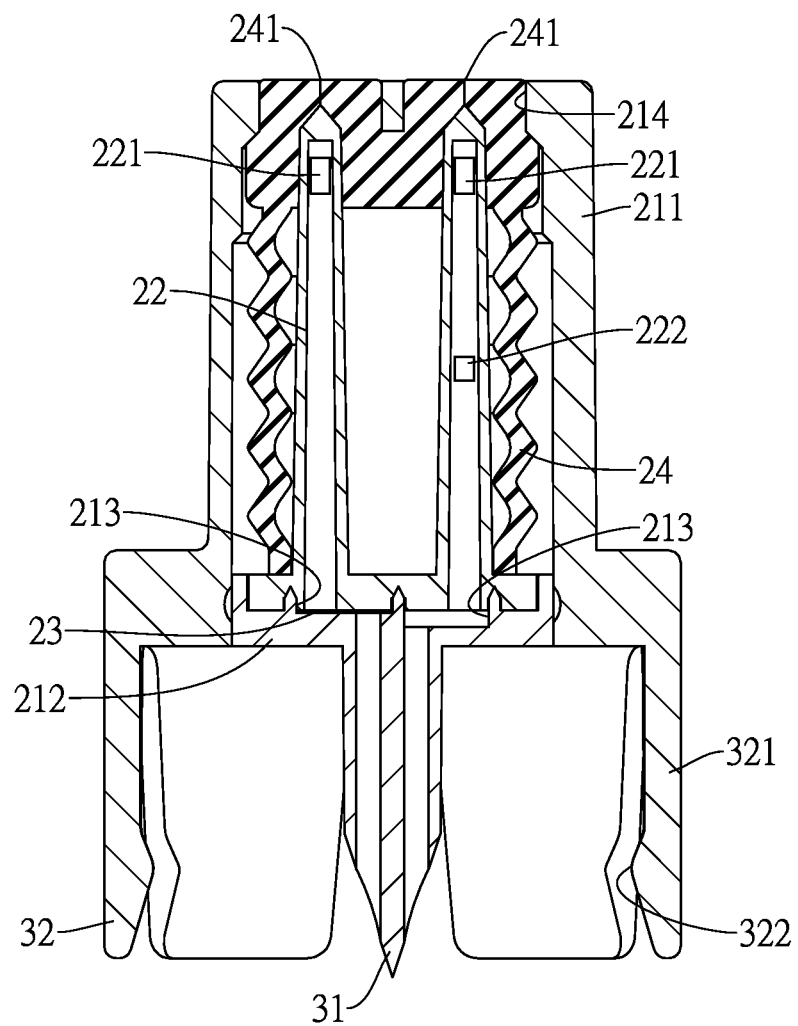
FIG. 5 is a front view in partial section of the connecting holder of the first embodiment of the present invention.

With reference to FIGS. 3 and 5 the connecting cover 21 has an upper shell 211, a base 212, at least one outer connecting hole 213, two adapting holes 214, and a fool-proof block 215. The upper shell 211 is a shell with an opening at a bottom end of the upper shell 211. The base 212 is disposed at a bottom of the connecting cover 21 and seals the opening of the upper shell 211. In the first embodiment, the base 212 and the upper shell 211 are connected with each other by adhesion, but the means of connection of the base 212 and the upper shell 211 are not limited thereto, and the base 212 and the upper shell 211 may be connected by other ways such as bayonetting or ultrasound.

The at least one outer connecting hole 213 is disposed on a bottom of the connecting cover 21. In the first embodiment, the amount of the at least one outer connecting hole 213 is two. The two outer connecting holes 213 are defined through the base 212 and are spaced from each other.

The two adapting holes 214 are defined through a top face of the connecting cover 21 and are spaced from each other. The fool-proof block 215 protrudes from an outer surface of the upper shell 211 of the connecting cover 21. The fool-proof block 215 is capable of slidably engaging with the fool-proof groove 116. In other words, when the syringe 10 and the connecting holder 20 are assembled, the syringe 10 and the connecting holder 20 can be successfully connected only when the fool-proof groove 116 is aligned with the fool-proof block 215.

With reference to FIGS. 3 and 5, the two piercing needles 22 are disposed within the connecting cover 21 and have two tips facing upward. Furthermore, the two piercing needles 22 are disposed on the base 212 of the connecting cover 21. The two piercing needles 22 are spaced from and are parallel to each other. One of the two piercing needles 22 is capable of being mounted through the rubber stopper 114 disposed within the air inlet tube 112 and entering the air inlet tube 112 via the slit 117 on the rubber stopper 114. The other one of the two piercing needles 22 is capable of being mounted through the rubber 124 disposed within the medication inlet tube 123 and entering the medication inlet tube 123 via the slit 125 of the rubber stopper 124. In the first embodiment, the piercing needles 22 are connected with the base 212 by adhesion. The connecting ways of the piercing needles 22 and the base 212 are not limited thereto, and the piercing needles 22 and the base 212 may be connected by other ways such as bayonetting or ultrasound.

With reference to FIG. 5, the piercing needles 22 further each respectively have an inner space and a first opening 221, the two inner spaces being independent from each other. The inner spaces of the piercing needles 22 respectively communicate with the two outer connecting holes 213. In other words, the inner space of each piercing needle 22 communicates with one of the outer connecting holes 213 by connecting a bottom end of the piercing needle 22 and a corresponding one of the outer connecting holes 213. The first opening 221 of each piercing needle 22 is disposed at a position adjacent to the tip of the piercing needle 22.

In addition, one of the piercing needles 22 that communicates with the medication inlet tube 123 further has a second opening 222. The second opening 222 is defined through an inner surface of the piercing needle 22 communicating with the medication inlet tube 123 and is disposed below the first opening 221 of the piercing needle 22.

With reference to FIGS. 3 and 5, the fluid stopper 23 is disposed within the connecting cover 21. More specifically, the fluid stopper 23 is disposed in the inner space of the piercing needle 22 that communicates with the air inlet tube 112. In the first embodiment, the fluid stopper 23 is disposed at the bottom end of the piercing needle 22 and is clamped between the bottom end of the piercing needle 22 and one of the outer connecting holes 213 corresponding to the piercing needle 22. In other words, the fluid stopper 23 is disposed inside the base 212. Additionally, in the first embodiment, the fluid stopper 23 is, but not limited to, a hydrophobic filter paper. The fluid stopper 23 may be implemented as other structures, as long as the fluid stopper 23 is capable of preventing fluid from flowing through the fluid stopper 23 and entering the piercing needle 22.

The elastic valve 24 is made of a flexible material that is compressible. The elastic valve 24 is disposed within the connecting cover 21 and selectively covers the two piercing needles 22. The elastic valve 24 has two notches 241 respectively disposed above the two piercing needles 22. The two notches 241 are normally open and are capable of being respectively pierced through by the two piercing needles 22. In the first embodiment, the elastic valve 24 and the two rubber stoppers 114, 124 are all made of rubber and have the same structures and achieve the purpose of being selectively opened by the two piercing needles 22 piercing through. The material and the structures of the two elastic valve 24 are not limited to the above, and the elastic valve 24 can be produced by other materials and the notches 241 can be implemented as other structures.

More specifically, in the first embodiment, the elastic valve 24 completely covers outer sides and top ends of the two piercing needles 22. When the connecting holder 20 is not connected with the syringe 10, the two piercing needles 22 are free from exposure out of the elastic valve 24.

The second connecting unit 25 is disposed on the connecting holder 20. The second connecting unit 25 corresponds to the first connecting unit 119 of the syringe 10 in position.

Figure 26:
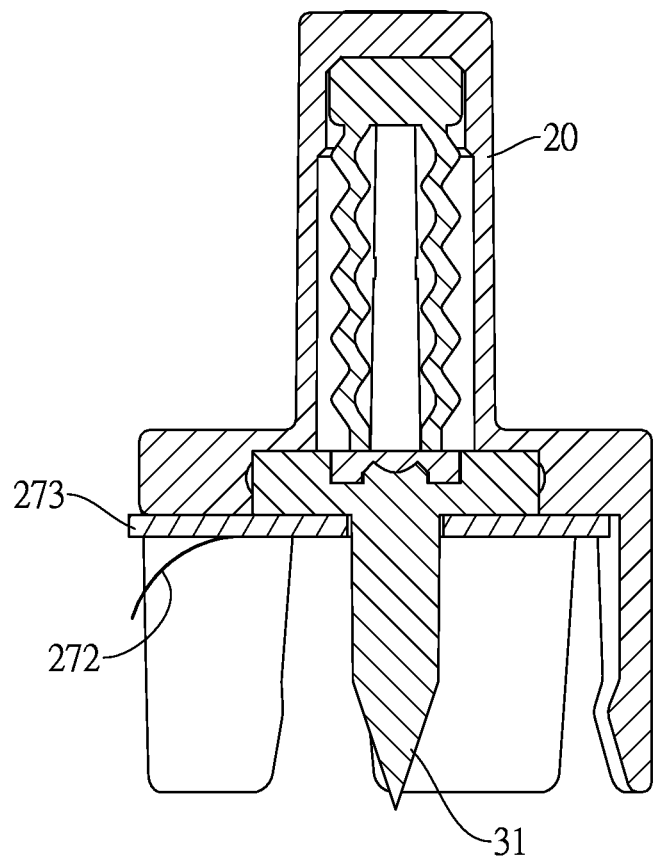
FIG. 26 is a cross sectional side view of FIG. 25.
Figure 27:
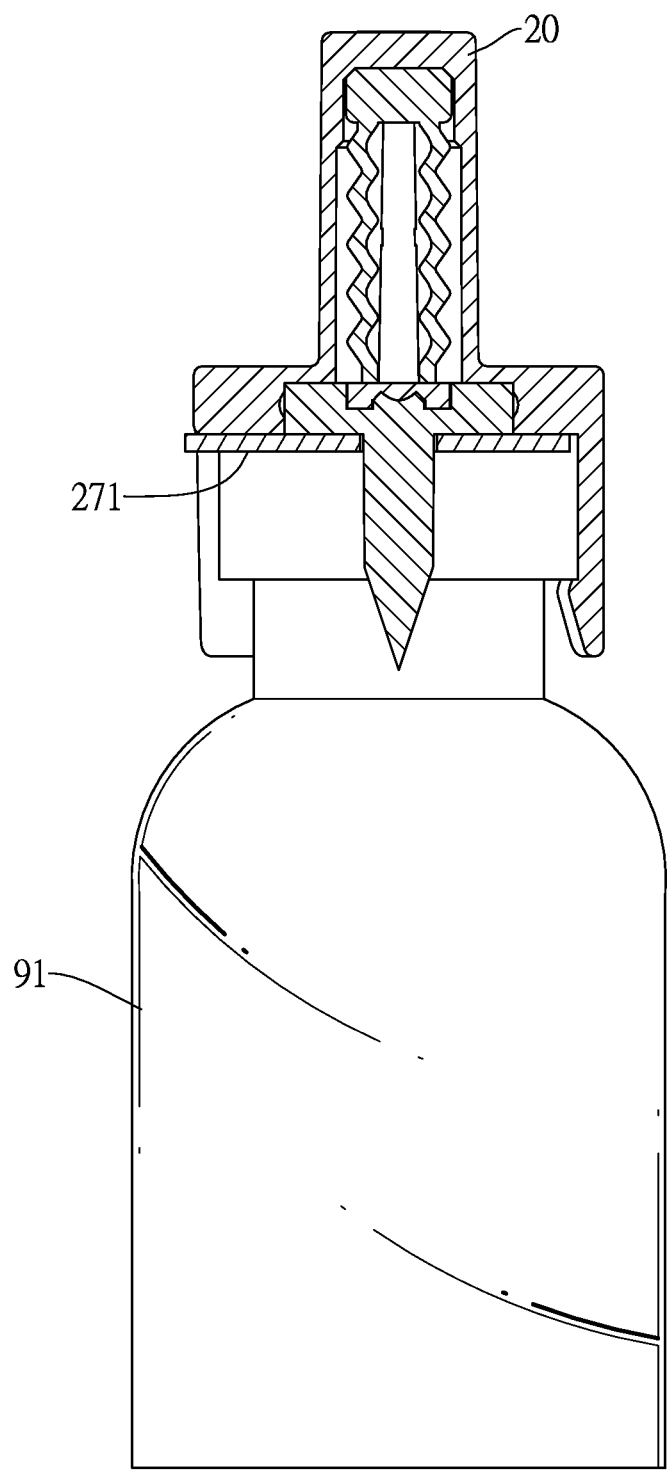
FIG. 27 is an operational side view in partial section of the connecting holder of the present invention and a phial.

With reference to FIGS. 25, 26, and 27, the leak-proof unit 27 is disposed within the connecting holder 20 and is mounted on and around a penetrating needle 31. The leak-proof unit 27 can prevent air and fluid from passing through. The leak-proof unit 27 has at least one adhesive face 271, a film 272, and at least one protruding tab 273. When the leak-proof unit 27 is assembled, the adhesive face 271 faces downward. The film 272 is detachably laminated on the at least one adhesive face 271. In the first embodiment, the leak-proof unit 27 is, but not limited to, a waterproof sticker with two adhesive faces 271 respectively disposed at both sides of the leak-proof unit 27.

With reference to FIGS. 16 to 24, the first connecting unit 119 and the second connecting unit 25 of the present invention have configurations, in terms of structure and means of connection, as follows.

Figure 16:
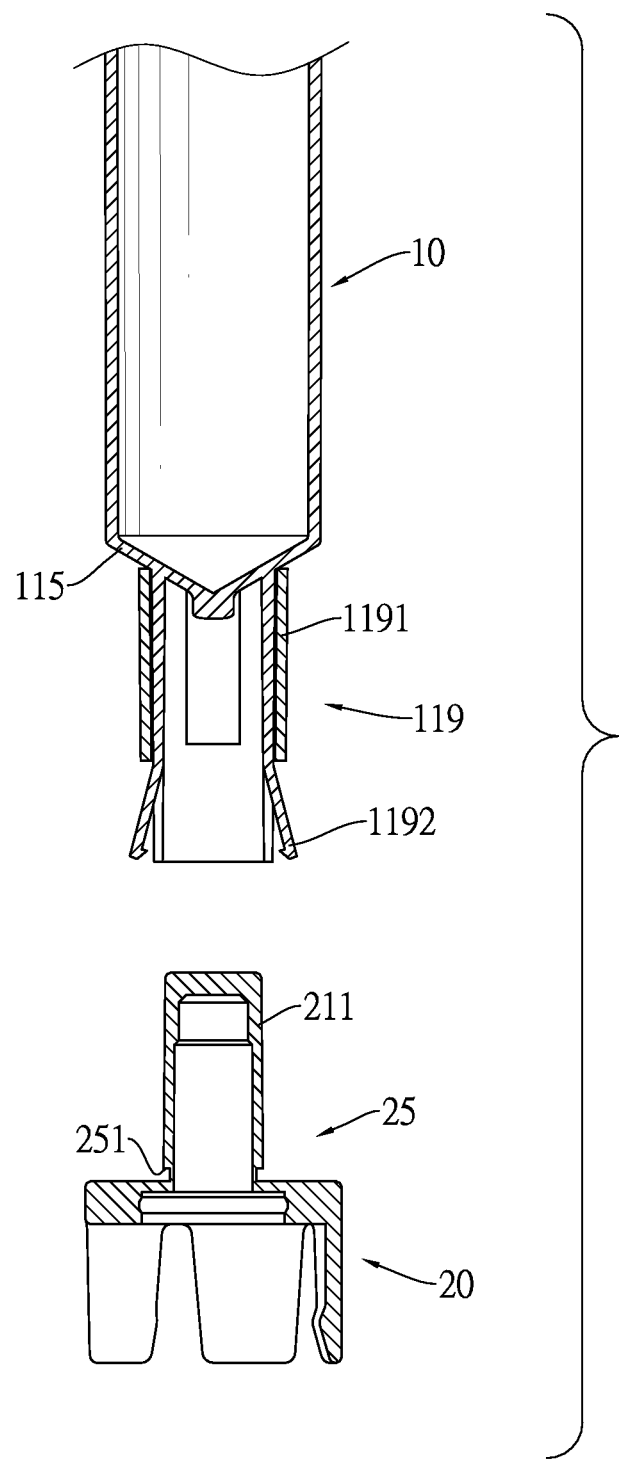
FIG. 16 is an exploded cross sectional side view of a first configuration of a connecting unit of the present invention.
Figure 17:
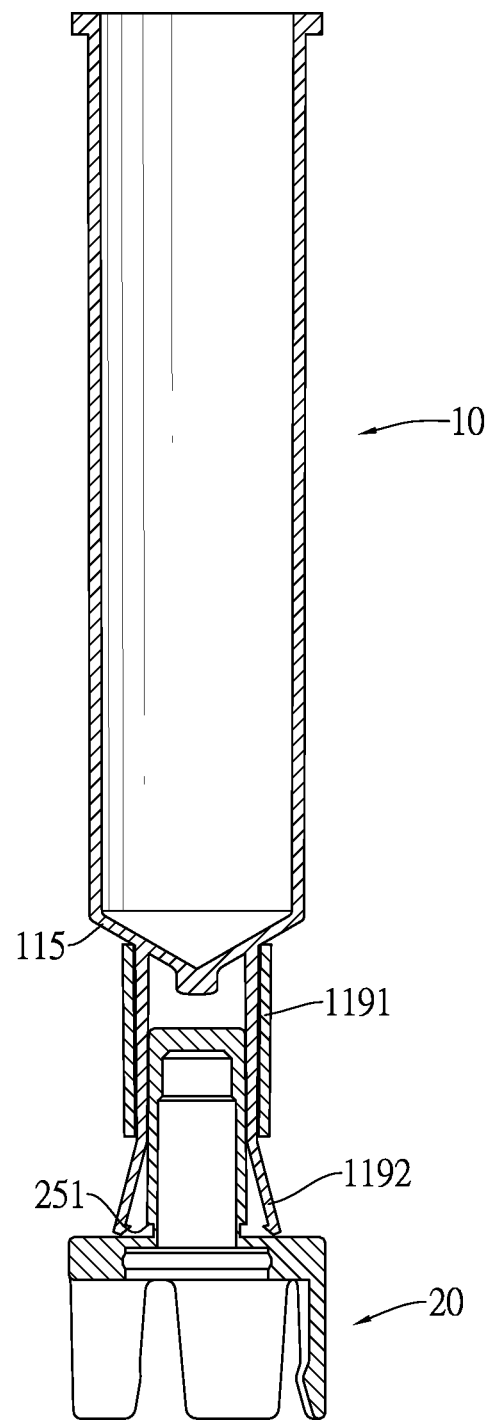
FIG. 17 is a first operational side view of FIG. 16.
Figure 18:
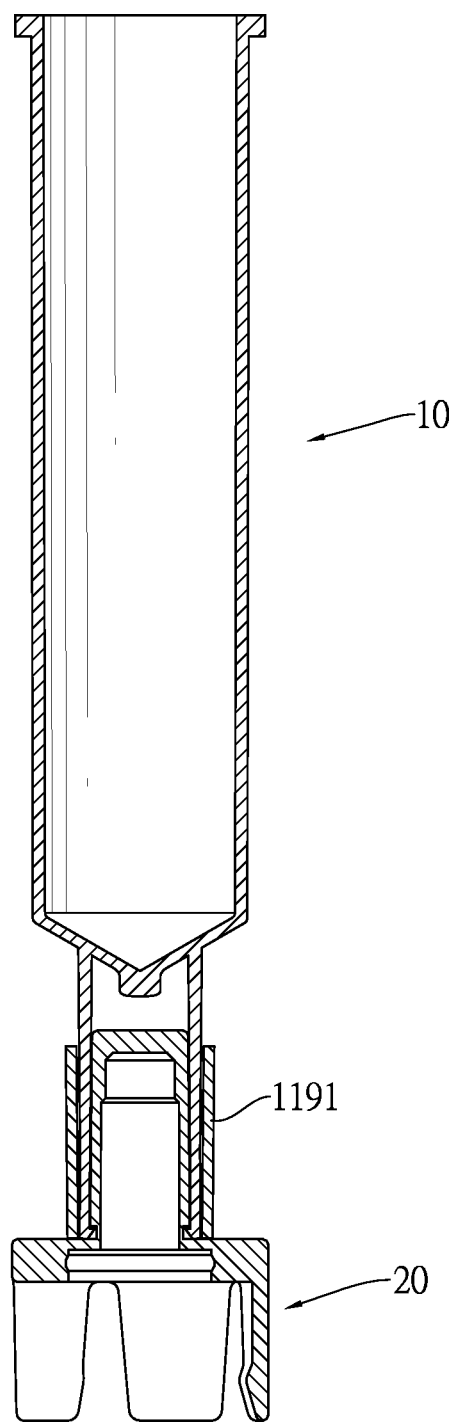
FIG. 18 is a second operational side view of FIG. 16.

With reference to FIGS. 16, 17, and 18, in a first configuration, the first connecting unit 119 has a sleeve 1191 and two elastic buckles 1192. The sleeve 1191 is sleeved on the outer cover 115. The two elastic buckles 1192 are respectively disposed at two sides of the outer cover 115 and are integrally formed on the outer cover 115. When under no subjecting forces, the elastic buckles 1192 bend outward with respect to the outer cover 115. More specifically, the two buckles 1192 are two hooks outward diverting from the two sides of the outer cover 115. With elasticity of the outer cover 115, the elastic buckles 1192 are bent outward.

In the first configuration, the second connecting unit 25 has two buckling recesses 251. The two buckling recesses 251 are disposed at a bottom of the upper shell 211 and are laterally formed in two opposite sides of the upper shell 211. The two buckling recesses 251 respectively correspond to the two elastic buckles 1192 in position.

An assembling method of the first connecting unit 119 and the second connecting unit 25 of the first configuration is described as follows. The outer barrel 11 is mounted around the connecting holder 20 at first. The elastic buckles 1192 are aligned with the buckling recesses 251. When the sleeve 1191 is downward pushed, the sleeve 1191 downward presses the elastic buckles 1192 at positions where the elastic buckles 1192 are outward bent to engage the elastic buckles 1192 with the buckling recesses 251 and to lock the syringe 10 to prevent the syringe 10 from moving up and down. When the user attempts to remove the syringe 10, the sleeve 1191 is upward slid, and the abutting between the sleeve 1191 and the elastic buckles 1192 is ended. The elastic buckles 1192 restore to a bending condition without being subjected to any forces, and the elastic buckles 1192 are detached from the buckling recesses 251. Therefore, the syringe 10 may be detached from the connecting holder 20.

Figure 19:
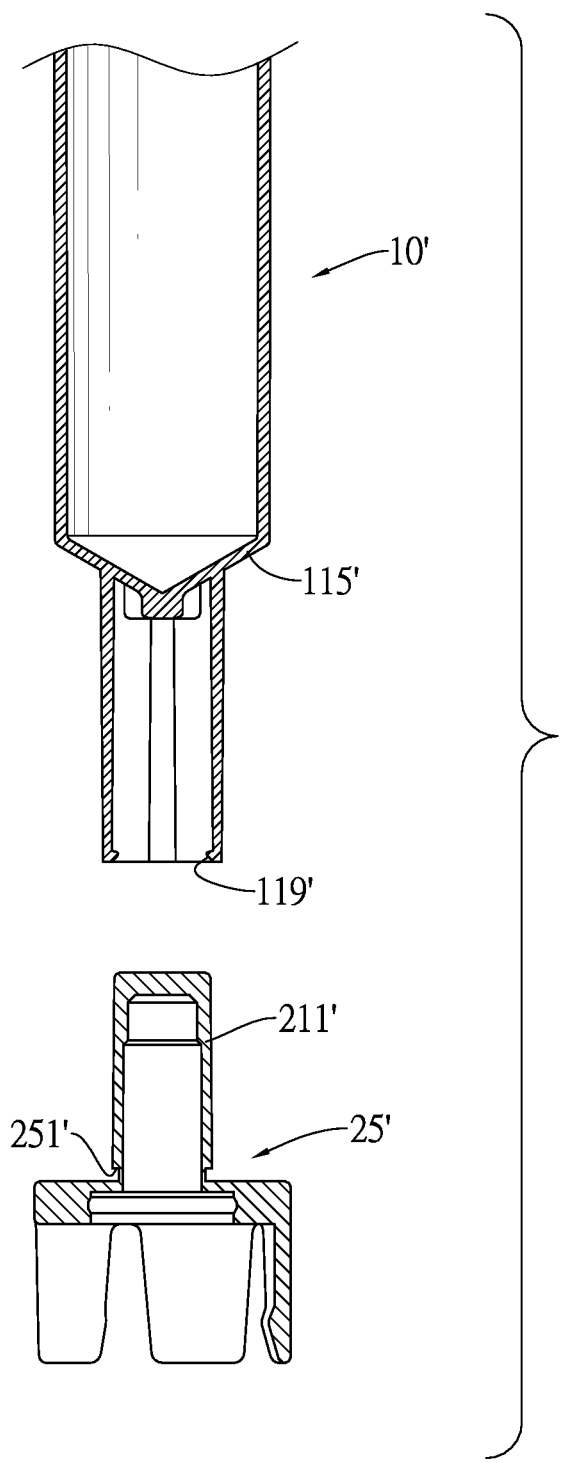
FIG. 19 is an exploded cross sectional side view of a second configuration of a connecting unit of the present invention.
Figure 20:
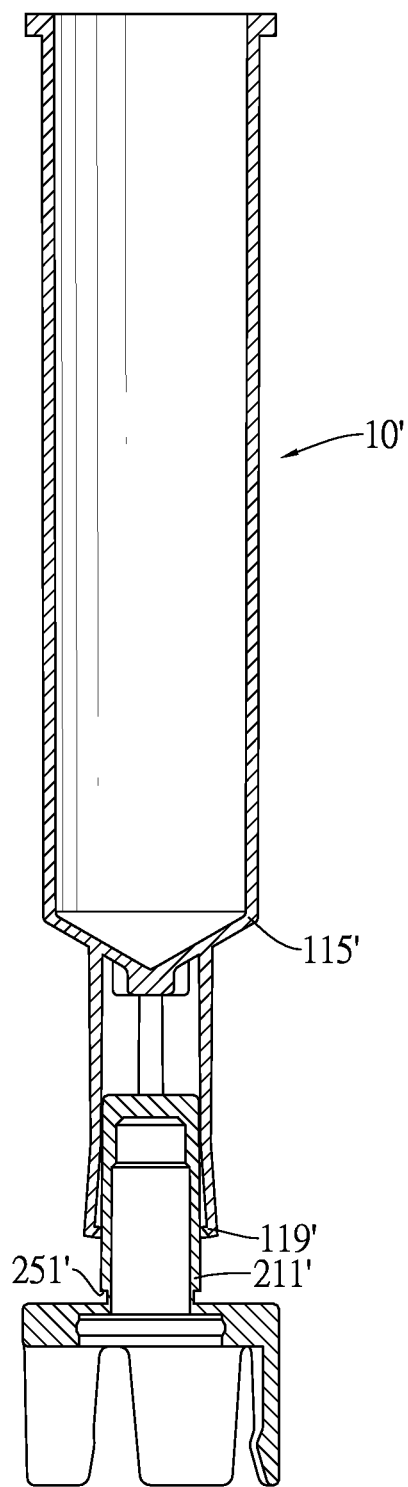
FIG. 20 is a first operational side view of FIG. 19.
Figure 21:
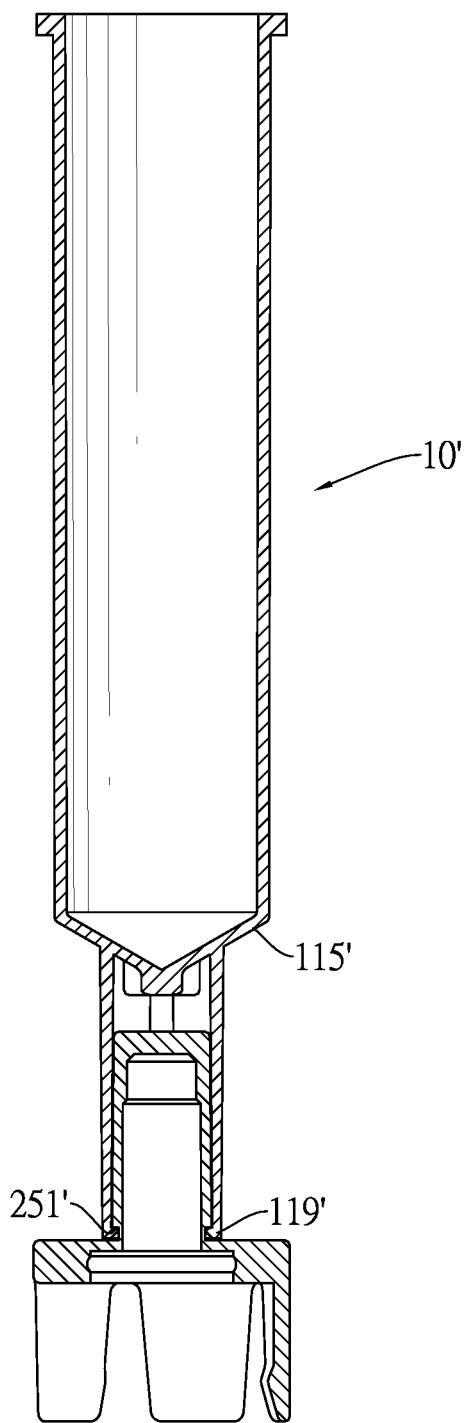
FIG. 21 is a second operational side view of FIG. 19.

With reference to FIGS. 19, 20, and 21, in a second configuration, the first connecting unit 119' is two bayonet hooks. The two bayonet hooks are integrally formed on the outer cover 115', and the two bayonet hooks protrude inward from the inner surface of the outer cover 115'. The second connecting unit 25' has two buckling recesses 251'. To fix the two bayonet hooks and the two buckling recesses 251', the outer cover 115' is downward mounted around the upper shell 211'. Since the shapes of the two bayonet hooks and the upper shell 211' are slightly different, the outer cover 115' is slightly deformed because the two bayonet hooks protrude inward. Deformation of the outer cover 115' remains when the outer cover 115' is continuously pressed downward. The two bayonet hooks are respectively engaged with the two buckling recesses 251' till the two bayonet hooks arrive at the two buckling recesses 251'. The outer cover 115' restores from deformation and achieves fixing. To remove the syringe 10 from the connecting holder 20, a slight upward force is applied to the syringe 10, and the two bayonet hooks are disengaged from the two buckling recesses 251'.

Figure 22:
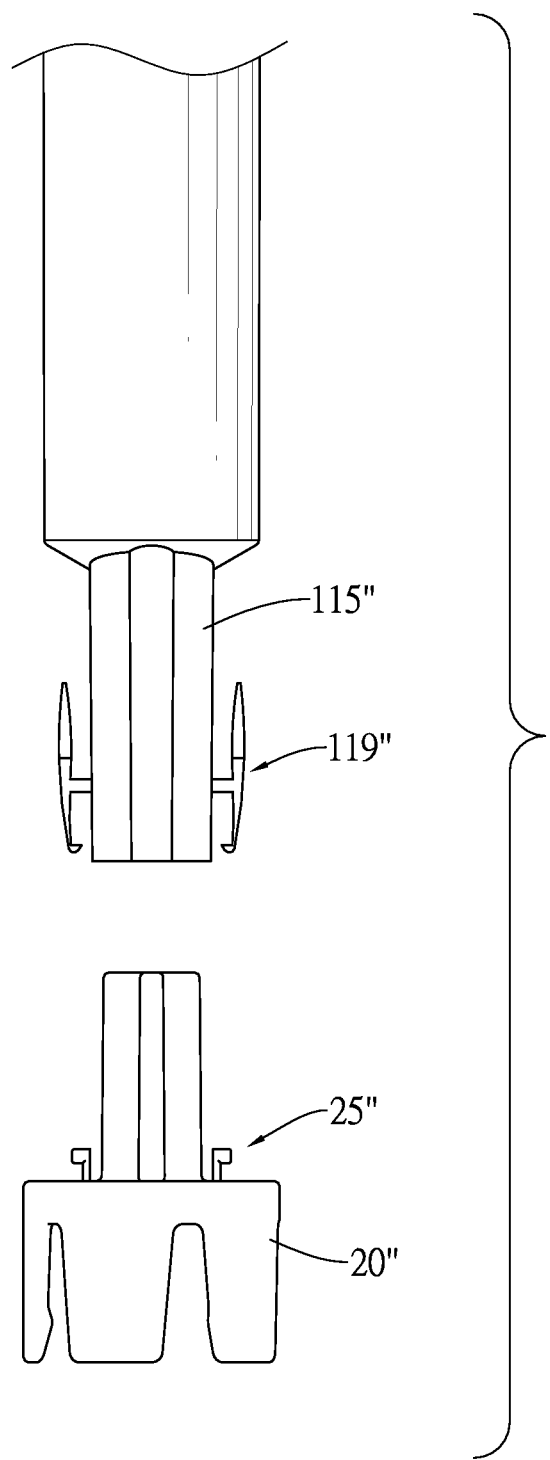
FIG. 22 is an exploded side view of a third configuration of a connecting unit of the present invention.
Figure 23:
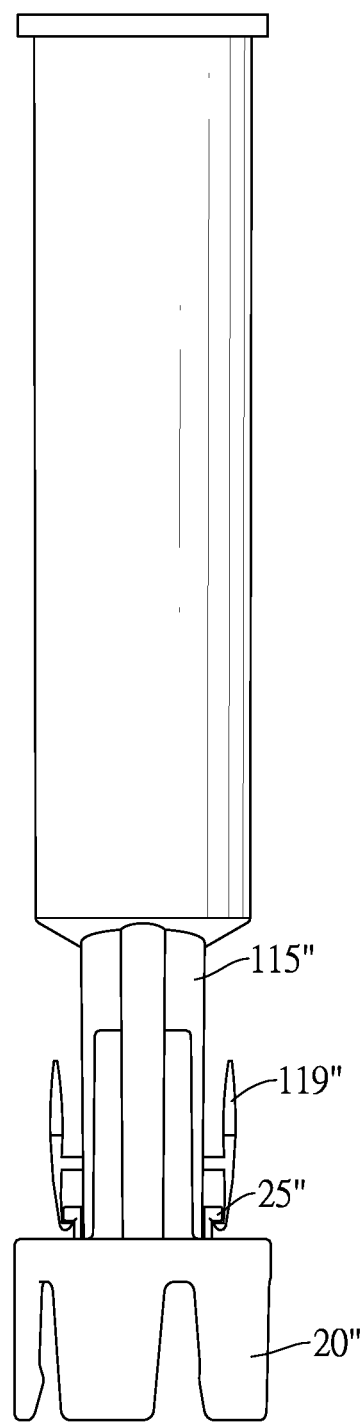
FIG. 23 is a first operational side view of FIG. 22.
Figure 24:
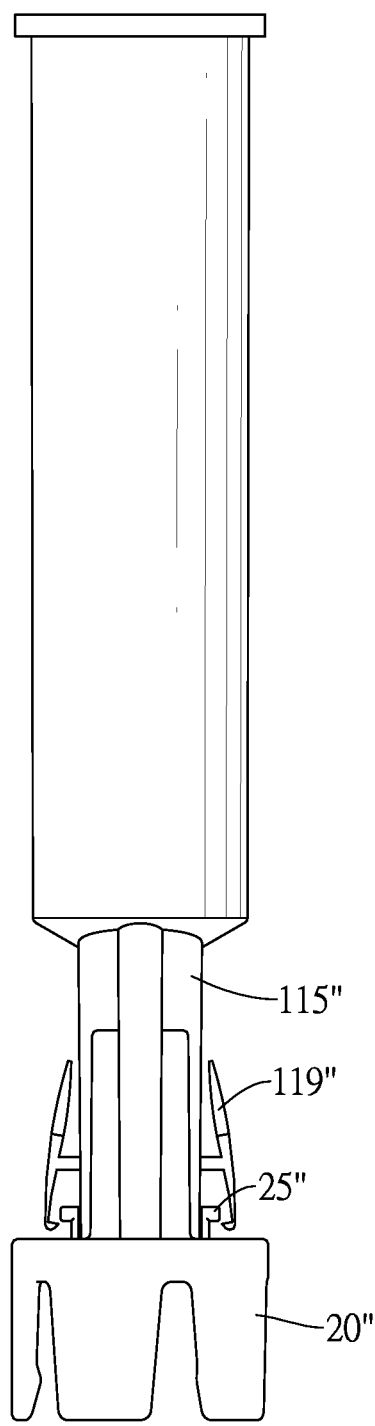
FIG. 24 is a second operational side view of FIG. 22.

With reference to FIGS. 22, 23, and 24, in a third configuration, the first connecting unit 119" is two engaging hooks. The two engaging hooks are laterally formed on the two opposite sides of the outer cover 115", respectively. Each engaging hook has a hook portion and a pressed portion. A linkage stick is disposed between the hook portion and the pressed portion to make them operate interactively. More specifically, when the pressed portion is pressed, the hook portion sweeps away from the outer cover 115", forming an expanding status as the elastic buckle 1192 in the first configuration. The second connecting unit 25" is two rods that are hook-like in shape. The two rods are formed on the connecting holder 20" and extend upward. Positions of the two second connecting units 25" correspond to positions of the two first connecting units 119". For fixing, the outer cover 115" is downward mounted on the connecting holder 20". The two first connecting units 119" downward and respectively engage with the two second connecting units 25". To remove the syringe 10 from the connecting holder 20", pressing the two pressed portions of the two first connecting units 119" will detach the first connecting units 119" from the two second connecting units 25".

Figure 15:
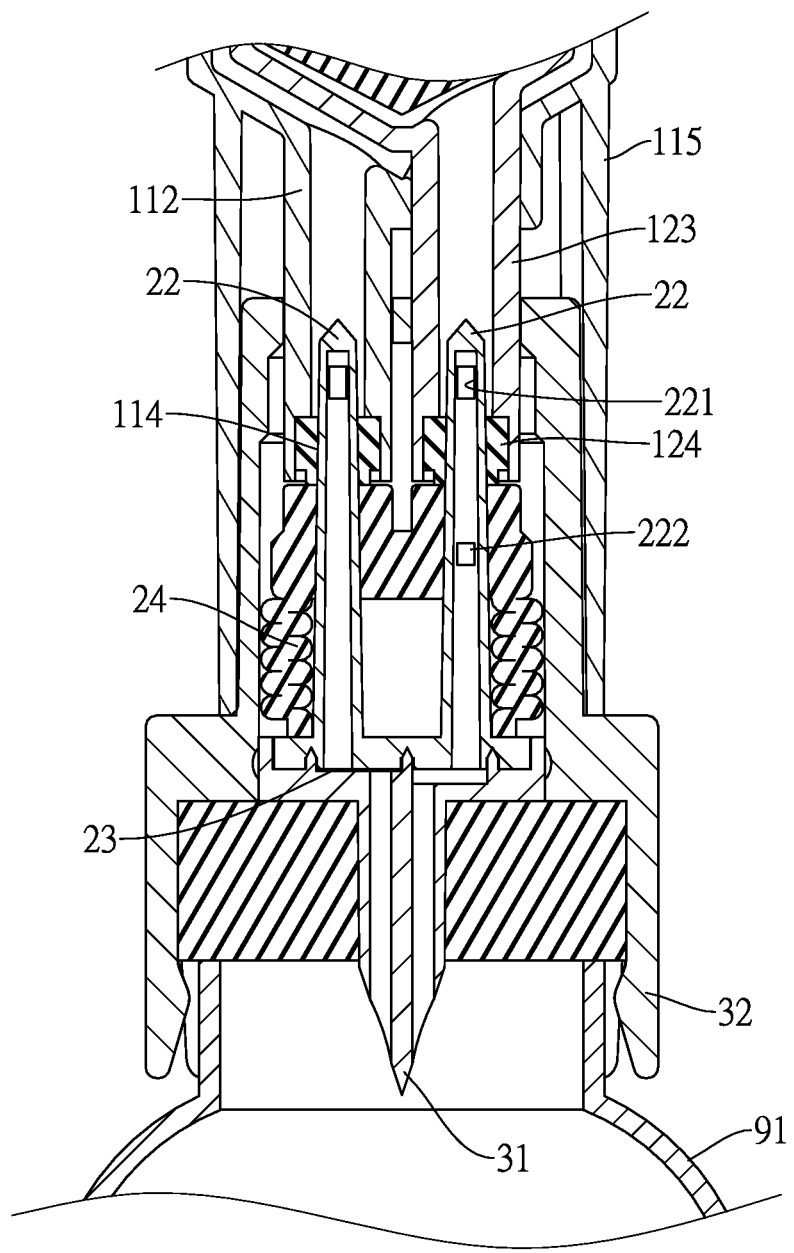
FIG. 15 is a partially enlarged side view of FIG. 12.

With reference to FIGS. 1, 5, and 15, in the first embodiment, the connecting holder 20 further has the penetrating needle 31 and a phial engaging portion 32. The penetrating needle 31 is disposed at the bottom of the connecting holder 20. More specifically, the penetrating needle 31 downward extends from a bottom face of the base 212 of the connecting cover 21 in a tip down manner. An inner space of the penetrating needle 31 communicates with the outer connecting holes 213. In the first embodiment, the penetrating needle 31 is integrally formed on the bottom face of the base 212. The outer connecting holes 213 extend through the penetrating needle 31. The inner space of the penetrating needle 31 communicates with the inner spaces of the two piercing needles 22 via the two outer connecting holes 213. The phial engaging portion 32 is annular and is connected to the bottom of the connecting cover 21. More specifically, the phial engaging portion 32 is integrally connected to the bottom face of the upper shell 211. The phial engaging portion 32 further has multiple phial engaging units 321. These phial engaging units 321 are disposed along an edge of a bottom end of the connecting cover 21 and perpendicularly and downward extend from the bottom of the connecting cover 21. Each one of the multiple phial engaging units 321 further has a phial hook 322 disposed at a bottom end of the phial engaging unit 321 and formed on an inner face of the phial engaging unit 321.

Figure 6:
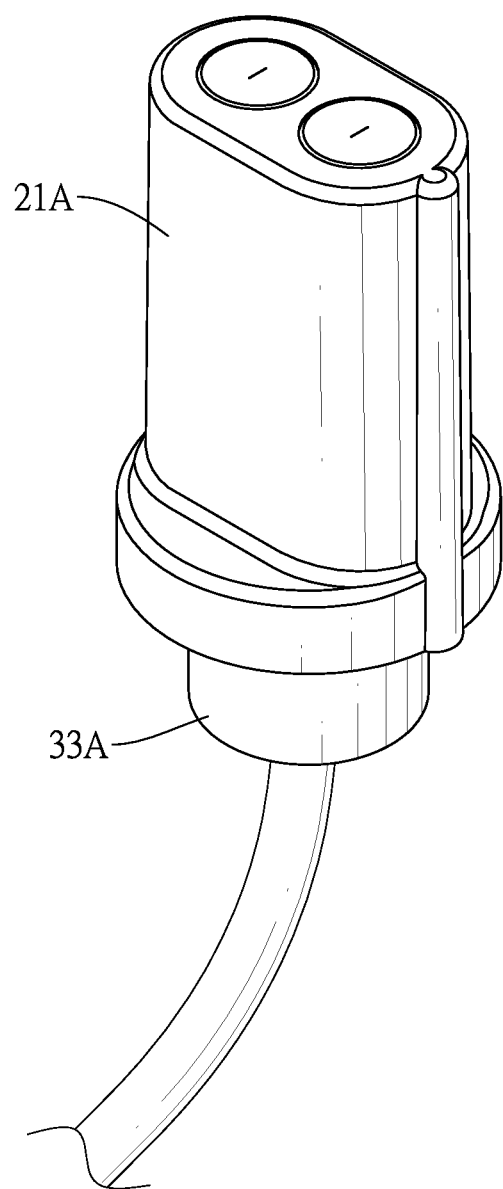
FIG. 6 is a perspective view showing a connection of a connecting holder of a second embodiment of the present invention and an infusion tube.
Figure 7:
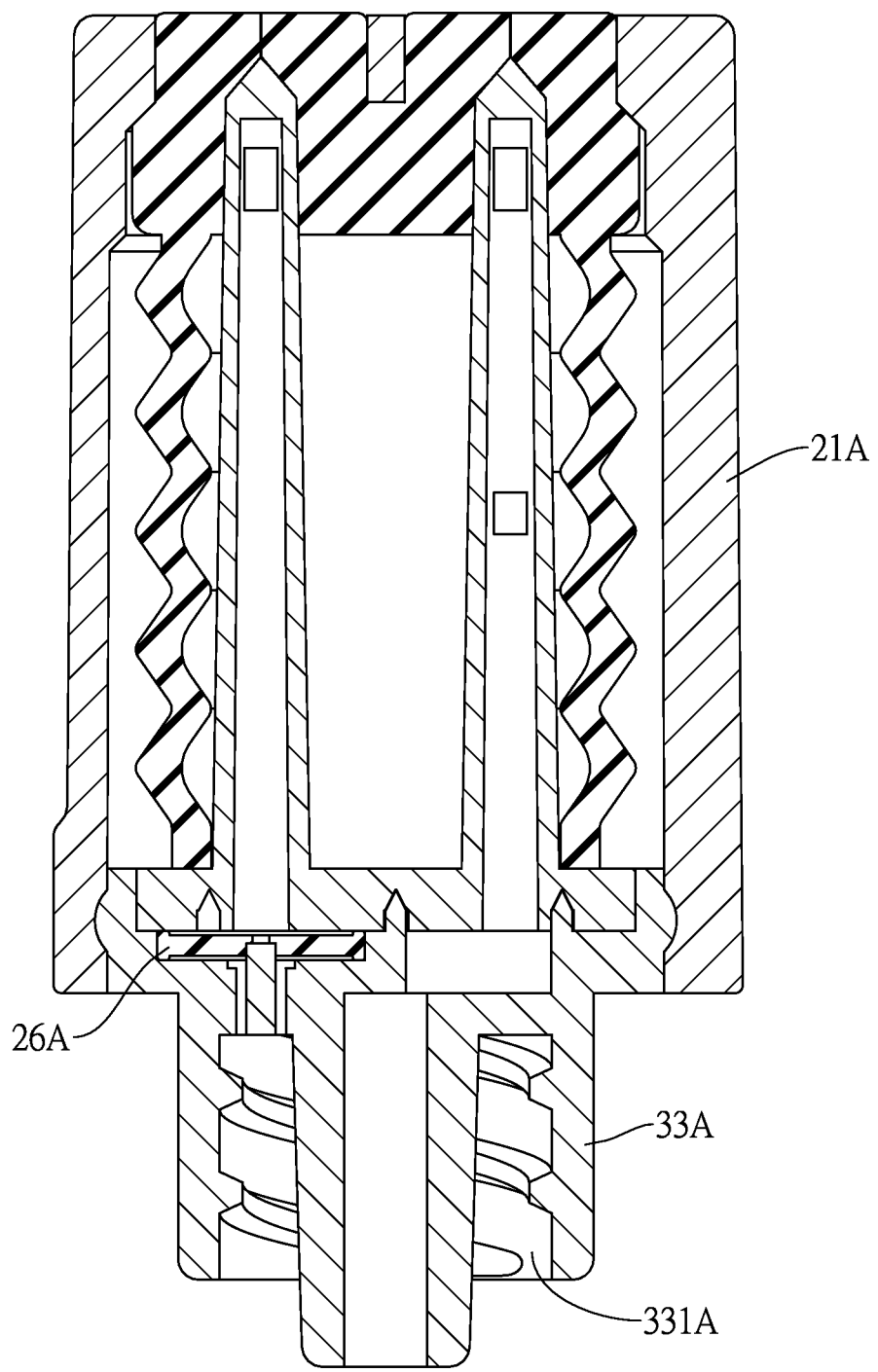
FIG. 7 is a front view in partial section of the connecting holder of the second embodiment of the present invention.

With reference to FIGS. 6 and 7, a second embodiment in accordance with the present invention is illustrated. The second embodiment and the first embodiment are substantially the same. In the second embodiment, the bottom of the connecting cover 21A is not connected by the penetrating needle 31 and the phial engaging portion 32 but connected by a connecting ring 33A instead. The connecting ring 33A is an annular wall that perpendicularly extends downward. An inner thread 331A is formed on an inner wall surface of the connecting ring 33A.

Figure 8:
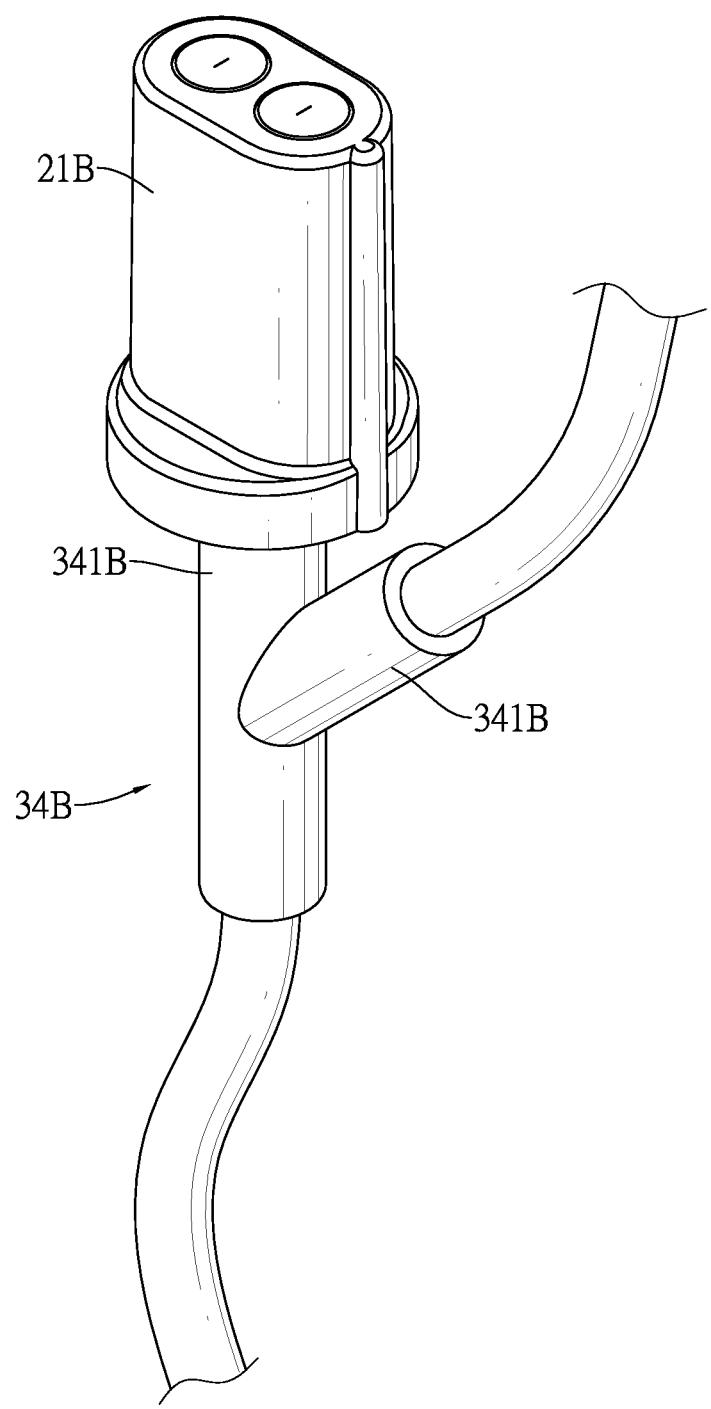
FIG. 8 is a perspective view showing a connection of a connecting holder of a third embodiment of the present invention and an infusion tube.
Figure 9:
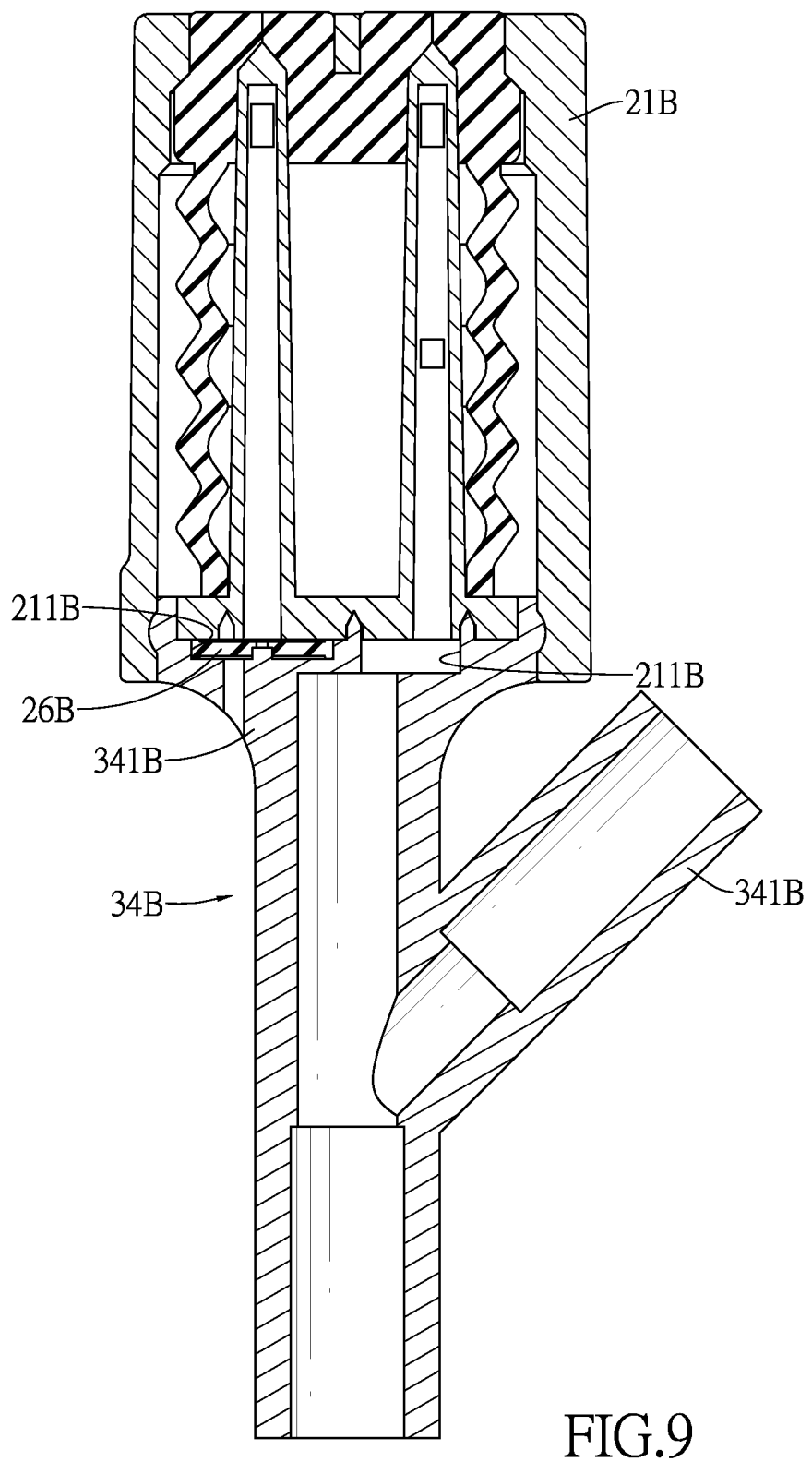
FIG. 9 is a front view in partial section of the connecting holder of the third embodiment of the present invention.

With reference to FIGS. 8 and 9, a third embodiment in accordance with the present invention is illustrated. The third embodiment is substantially same as the first embodiment. In the third embodiment, instead of being connected by the penetrating needle 31 and the phial engaging portion 32, the bottom of the connecting cover 21B is connected by a Y connector 34B. The Y connector 34B has two branches 341B disposed at a top of the Y connector 34B. One of the two branches 341B is connected to the bottom of the connecting cover 21B and communicates with the outer connecting holes 213B.

Figure 10:
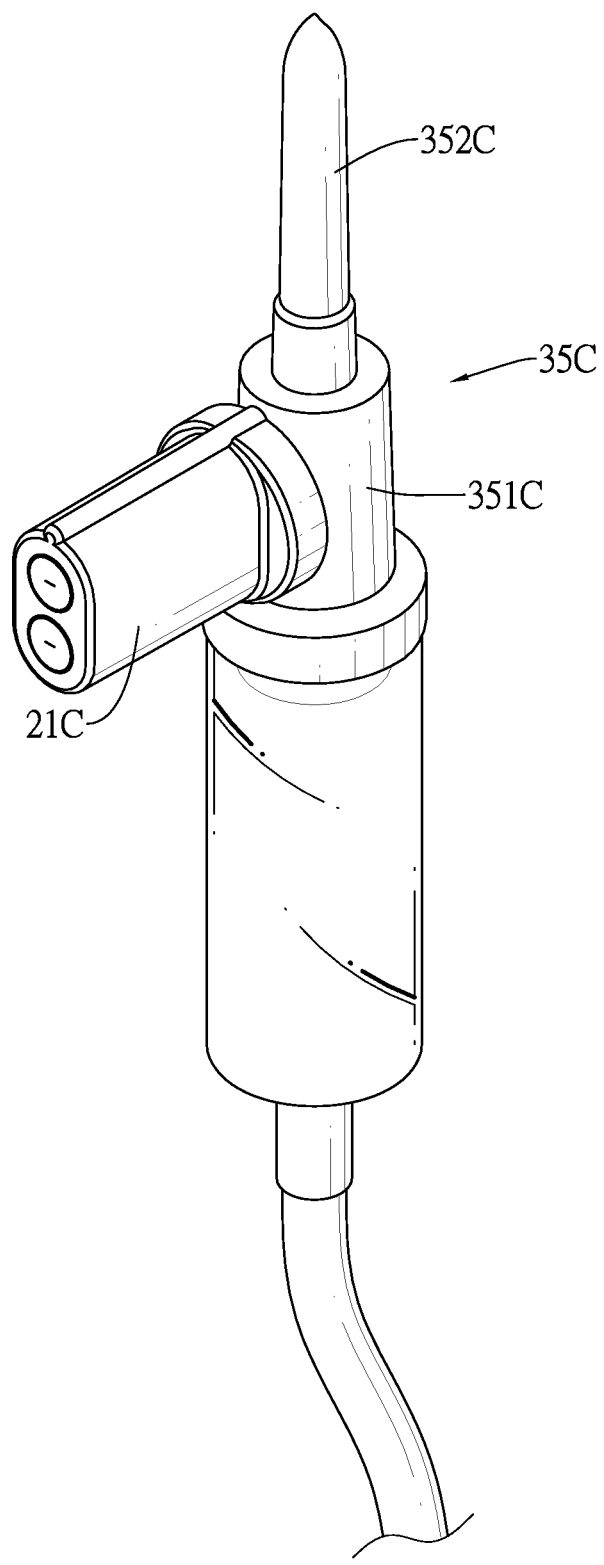
FIG. 10 is a perspective view showing a connection of a connecting holder of a fourth embodiment of the present invention and an infusion tube.
Figure 11:
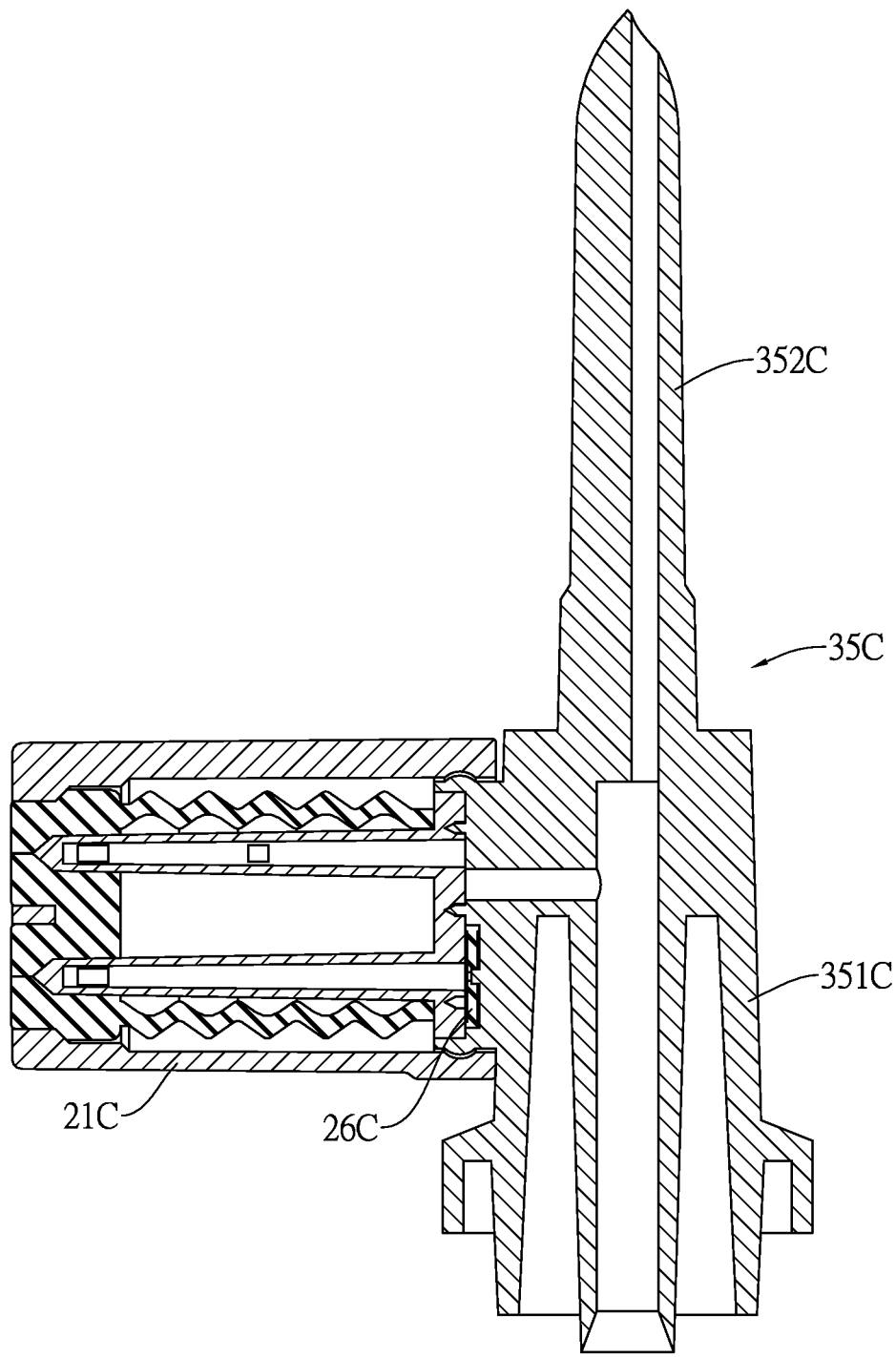
FIG. 11 is a front view in partial section of the connecting holder of the fourth embodiment of the present invention.

With reference to FIGS. 10 and 11, a fourth embodiment in accordance with the present invention is illustrated. The fourth embodiment and the first embodiment are substantially the same. In the fourth embodiment, instead of being connected by the penetrating needle 31 and the phial engaging portion 32, the bottom of the connecting cover 21C is connected to an intravenous administration set 35C. The intravenous administration set 35C has an adaptor 351C and a spike 352C. A lateral wall of the adaptor 351C is connected to the bottom of the connecting cover 21C. The inside of the adaptor 351C communicates with the outer connecting holes 213C, and the spike 352C is connected to the adaptor 351C. An inner space of the adaptor 351C and an inner space of the spike 352C communicate with each other.

Operation of the present invention is illustrated as follows.

Figure 12:
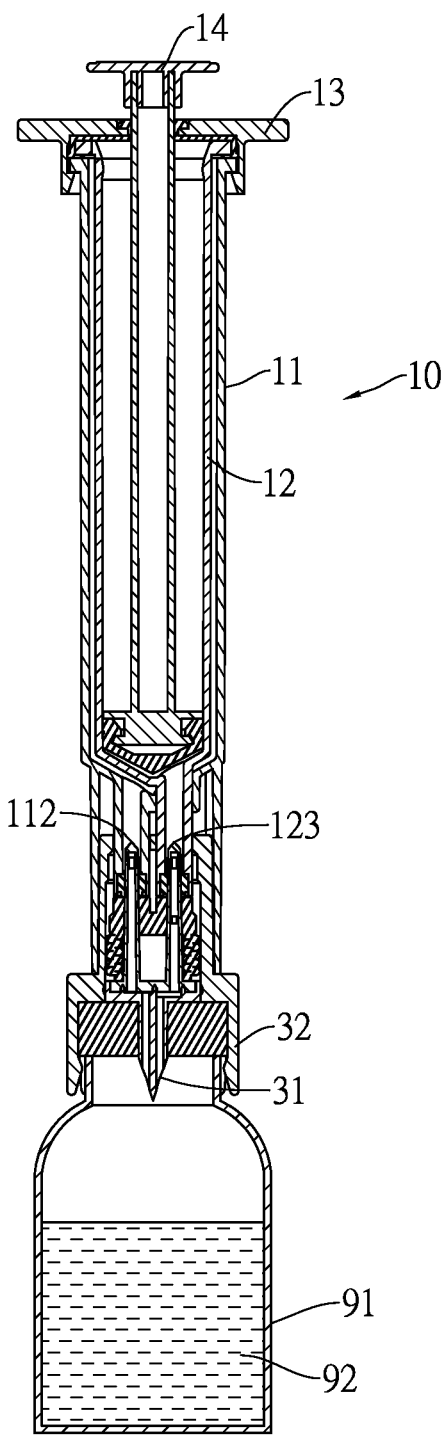
FIG. 12 is a first operational side view of withdrawing medicine by the first embodiment.

With reference to FIGS. 4, 5, and 12, in the first embodiment, the connecting holder 20 is designed for withdrawing medicine from a phial. A sealing film on a top end of a phial 91 is pierced through by the penetrating needle 31 that pierces downward, such that the connecting holder 20 communicates with an inner space of the phial 91. At this time, the phial engaging portion 32 is fixed to a bottom rim of the phial 91. Therefore, the connecting holder 20 is firmly fixed to the top end of the phial 91.

With reference to FIGS. 12, 25, 26, and 27, the film 272 of the leak-proof unit 27 is removed before the connecting holder 20 is downward connected to the phial 91. The film 272 can be easily removed because the protruding tab 273 protrudes out of the connecting holder 20. After the film 272 is removed, the connecting holder 20 is downward pressed after facing the adhesive face 271 toward the phial 91. The adhesive face 271 is firmly fixed to a mouth of the phial 91. Being waterproof and airtight, the leak-proof unit 27 prevents leakage of the medicine 92 contained inside the phial 91. The film 272 is to prevent the adhesive face 272 from mistakenly adhering to other objects before the connecting holder 20 is adhered to the phial 91.

With reference to FIGS. 1, 12, and 15, after the connecting holder 20 is fixed to the phial 91, the syringe 10 is connected to the connecting holder 20 in a direction that the outer cover 115 is aligned with the connecting holder 20. The syringe 10 and the connecting holder 20 have to be connected to each other in a specific orientation for the two piercing needles 22 to be respectively inserted into the air inlet tube 112 of the outer barrel 11 and the medication inlet tube 123 of the inner barrel 12. Therefore, the fool-proof groove 116 formed in the inner surface of the outer cover 115 and the fool-proof block 215 protruding from the outer surface of the connecting cover 21 prevent the syringe 10 from inadvertent insertion into the connecting holder 20 in a reverse manner.

With reference to FIGS. 12 and 15, when the syringe 10 is connected to the connecting holder 20, the air inlet tube 112 and the medication inlet tube 123 extend through the adapting holes 214 disposed at the top end of the connecting cover 21. The air inlet tube 112 and the medication inlet tube 123 enter inside the connecting cover 21 at first and then downward abut the elastic valve 24. When the air inlet tube 112 and the medication inlet tube 123 are gradually pushed downward, the elastic valve 24 is gradually compressed accordingly. Therefore, the two piercing needles 22 respectively pierce through the two notches 241 of the elastic valve 24 and continuously pierce through the two rubber stoppers 114, 124. The two piercing needles 22 respectively enter inside the air inlet tube 112 and the medication inlet tube 123.

Figure 13:
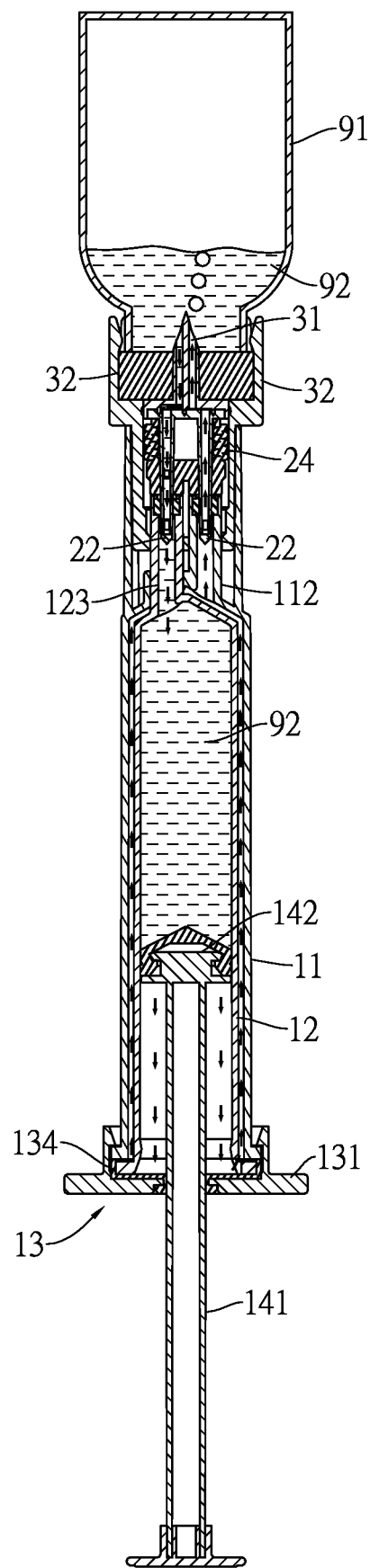
FIG. 13 is a second operational side view of withdrawing medicine by the first embodiment.

With reference to FIG. 13, after the syringe 10 is connected to the connecting holder 20, the present invention and the phial 91 connected to the present invention are held upside down. The plunger 14 is slowly pulled away from the phial 91. Upon each pull of the plunger 14, the piston 142 of the plunger 14 moving away from the phial 91 increases a volume between the piston 142 and a bottom of the inner barrel 12. A volume between the piston 142 and the airtight cap 13 is decreased accordingly. Air originally existing between the piston 142 and the airtight cap 13 enters a space between the outer barrel 11 and the inner barrel 12 and then enters the phial 91. With the complementary increase and decrease of volumes, the medicine 92 inside the phial 91 downward passes through the penetrating needle 31 and flows into the present invention due to an additional air pressure.

When the medicine 92 enters the present invention, air inside the phial 91 and gas volatized from the medicine 92 float above the medicine 92 because the present invention is posed upside down and is free from moving downward and entering the syringe 10. Gas volatized from the medicine 92 and air entering the phial 91 are mixed up and turn into mixed gas. In addition, in order to completely separate the medicine 92 and the mixed gas, the fluid stopper 23 is equipped with one of the two piercing needles 22. When the medicine 92 is to pass through the piercing needle 22 equipped with the fluid stopper 23, the medicine 92 is blocked by the fluid stopper 23 and cannot pass through the piercing needle 22. The piercing needle 22 equipped with the fluid stopper 23 only allows the mixed gas to pass through. Moreover, the piercing needle 22, which only allows passage of mixed gas, communicates with the air inlet tube 112 of the outer barrel 11. Therefore, the mixed gas enters the air inlet tube 112, flows along an inner space between the outer barrel 11 and the inner barrel 12, and continuously flows toward the airtight cap 13. The mixed gas further enters a space between the piston 142 and the airtight cap 13 via the vent 122 of the inner barrel 12 even when entering the syringe 10.

At the same time, the medicine 92 passes through the other one of the two piercing needles 22, enters the medication inlet tube 123 of the inner barrel 12, and enters the inner barrel 12, thereby achieving the purpose of separating liquid and gas during medicine withdrawal.

Figure 14:
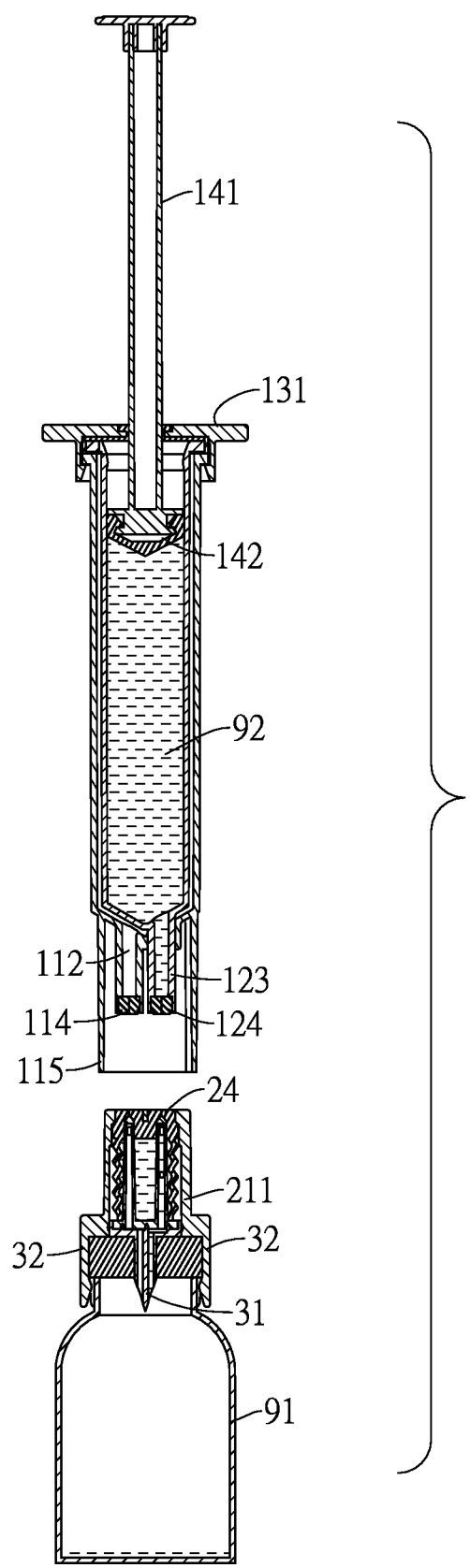
FIG. 14 is a third operational side view of withdrawing medicine by the first embodiment.

With reference to FIG. 14, after withdrawal of medicine, the syringe 10 of the present invention is removed from the connecting holder 20. Upon removal of the syringe 10, the two piercing needles 22 respectively make the slits 117, 125 of the rubber stopper 114, 124 close again. Therefore, both the medicine 92 and mixed gas inside the syringe 10 are prevented from accidental leakage. Meanwhile, when the piercing needle 22 passed through by the medicine 92 is removed, the second opening 222, by negative pressure, sufficiently draws back the medicine 92 remaining on a lateral wall of the piercing needle 22 and on the elastic valve 24 into an inner space of the elastic valve 24. Consequently, sealing of the present invention is enhanced. The first opening 221 and the second opening 222 are structurally identical but are disposed at different positions. Therefore, when the syringe 10 is removed, the remaining medicine 92 is not only drawn via the second opening 222, but also via the first opening 221 when the remaining medicine 92 passes through the first opening 221 to sufficiently draw back the remaining medicine.

With reference to FIGS. 6 and 7, in the second embodiment, the connecting holder 20A is adapted for the syringe 10A that has completed medicine withdrawal. In reversing the operation steps mentioned above, the medicine is injected into a patient via the connecting holder 20A. The connecting ring 33A disposed at a bottom of the connecting holder 20A can be readily connected to an infusion tube by screw-threading. In the second embodiment, a position originally occupied by the fluid stopper 23 is occupied by a check valve 26A instead. The check valve 26A is capable of blocking air flow toward an injecting direction, thereby preventing pumping air into the patient.

With reference to FIGS. 8 and 9, in the third embodiment, the bottom of the connecting holder 20B communicates with one of the branches 341B of the Y connector 34B. The other one of the branches 341B is capable of communicating with a drainage bap for intravenous injection. Two bottom ends of the two branches 341B are confluent and communicate with a same tube for transmitting medication inside the patient. The medicine for intravenous injection and the medicine stored within the drainage bag can be transmitted inside the patient together via the connecting holder 20B of the third embodiment. In addition, same as the second embodiment, in the third embodiment, the position originally occupied by the fluid stopper 23 is occupied by a check valve 26B instead because the third embodiment is adapted for injecting medicine into the patient. The check valve 26B is capable of blocking air flow toward an injecting direction and thereby preventing pumping air into the patient.

With reference to FIGS. 10 and 11, a common point of the third and fourth embodiments is that the third and fourth embodiments are both designed for intravenous injection. However, in the fourth embodiment, the spike 352C directly communicates with a phial or a drainage bag. One end of the adaptor 351C is connected to the syringe 10. After the medicine inside the present invention is mixed up with the medicine inside the phial or the drainage bag and turned into a mixed medicine, the mixed medicine is transmitted, dripping downward to the patient. In other words, in the third embodiment, the medicine inside the present invention is added and the medicine inside the drainage bag drips simultaneously. In the fourth embodiment, the medicine inside the present invention and the medicine inside the phial or the drainage bag are mixed up to become the mixed medicine before transmitting inside the patient. In addition, the fluid stopper 23 is replaced by the check valve 26C as the fourth embodiment is configured for injecting medicine into the patient.

In a process of applying the present invention to insert the phial, and to access and withdraw medicine, dangerous needles are completely kept unexposed, so the present invention is highly safe; meanwhile, the medicine and air totally flow inside the connecting cover 21 of the connecting holder 20. After the syringe 10 is removed, the syringe 10 and the connecting holder 20 are sealed again, so the present invention is highly sealed during medicine withdrawal, and the clinical staff can avoid getting stained by the medicine; in addition, the present invention can be easily inserted and readily removed, promoting the efficiency of usage. In conclusion, the improvements of structures for dispensing and administering medicine are provided with safety, convenience, and quickness for use.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A sealed medication dispensing and administering device, characterized in that the sealed medication dispensing and administering device comprises:
    a syringe having
        an outer barrel having an air inlet tube, a rubber stopper, and a connecting hole; the air inlet tube downward extending from a lower face of the outer barrel; the rubber stopper disposed within the air inlet tube and disposed at a position adjacent to an opening that is at a bottom end of the air inlet tube; the rubber stopper having a slit that is normally closed; and the connecting hole defined through the lower face of the outer barrel and being spaced from the air inlet tube;
        an inner barrel inserted inside the outer barrel and having a vent, a medication inlet tube, and a rubber stopper; the vent disposed on an inner surface of the inner barrel and communicating with an inner space of the inner barrel and an inner space of the outer barrel; the medication inlet tube disposed on a lower face of the inner barrel and mounted through the connecting hole of the outer barrel; the rubber stopper of the inner barrel disposed within the medication inlet tube and disposed at a position adjacent to an opening that is at a bottom end of the medication inlet tube; and the rubber stopper of the inner barrel having a slit that is normally closed; and
        a plunger inserted within the outer barrel and the inner barrel and being moveable up and down; the plunger having a piston disposed at a bottom end of the plunger; and the piston longitudinally dividing the inner space of the inner barrel into two parts that are free from communicating with each other;
    a connecting holder detachably connected to the syringe and having
        a connecting cover having at least one outer connecting hole; and
        two piercing needles disposed within the connecting cover and respectively having two tips facing upward; the two piercing needles respectively and selectively piercing through the slit of the rubber stopper disposed within the medication inlet tube and the slit of the rubber stopper disposed within the air inlet tube; the piercing needles each having a respective inner space being independent from each other and a first opening; the inner space of each piercing needle communicating with the at least one outer connecting hole of the connecting cover; and the first opening disposed at the tip of the piercing needle;
    an elastic valve made of a flexible material that is compressible; the elastic valve disposed within the connecting cover; the elastic valve selectively covering the two piercing needles; the elastic valve having two notches; the two notches respectively disposed above the two piercing needles, and the two notches normally being open and respectively and selectively pierced through by the two piercing needles; and
    a fluid stopper disposed within the connecting cover and corresponding to the inner space of one of the two piercing needles that corresponds to the air inlet tube in position.

2. The sealed medication dispensing and administering device as claimed in claim 1, wherein the fluid stopper is a hydrophobic filter paper.

3. The sealed medication dispensing and administering device as claimed in claim 1 or 2, wherein said one of the two piercing needles corresponding to the air inlet tube further has a second opening, and the second opening is defined through an inner surface of said piercing needle and is disposed below the first opening.

4. The sealed medication dispensing and administering device as claimed in claim 1 or 2, wherein
    the outer barrel further has an outer cover and a fool-proof groove; the outer cover is annular and perpendicularly extends from the lower face of the outer barrel; and the fool-proof groove is formed in an inner surface of the outer cover; and
    the connecting cover of the connecting holder further has a fool-proof block; the fool-proof block protrudes from the connecting cover; and the fool-proof block is capable of slidably engaging with the fool-proof groove.

5. The sealed medication dispensing and administering device as claimed in claim 1 or 2, wherein
    the outer barrel further has an outer barrel opening, and the outer barrel opening is defined through a top face of the outer barrel;
    the inner barrel further has an inner barrel opening, the inner barrel opening is defined through a top face of the inner barrel, and the inner barrel is inserted inside the outer barrel via the outer barrel opening;
    the syringe further has an airtight cap with an airtight ring; the airtight cap is disposed on the top face of the inner barrel and the top face of the outer barrel; the airtight cap covers the outer barrel opening and the inner barrel opening; and the airtight cap clamps and fixes the outer barrel and the inner barrel; and the airtight ring is disposed between and abuts against a bottom face of the airtight cap and the top face of the inner barrel.

6. The sealed medication dispensing and administering device as claimed in claim 5, wherein the connecting holder further has a leak-proof unit disposed within the connecting holder.

7. The sealed medication dispensing and administering device as claimed in claim 1 or 2, wherein
the outer barrel further has a first connecting unit; and
the connecting cover further has a second connecting unit detachably connected to the first connecting unit.

8. The sealed medication dispensing and administering device as claimed in claim 7 wherein
the first connecting unit has a sleeve and two elastic buckles; the sleeve is sleeved on the outer barrel and is slidable up and down; and the two elastic buckles are disposed at a bottom of the outer barrel, formed on two opposite lateral sides of the outer barrel, and bent outward with respect to the outer barrel; and
the second connecting unit has two buckling recesses; the two buckling recesses laterally defined in the connecting cover; and positions of the two buckling recesses respectively correspond to positions of the two elastic buckles,
wherein when the outer barrel is connected to the connecting holder, the sleeve slides downward and abuts the two elastic buckles such that the two elastic buckles respectively engage with the two buckling recesses.

9. The sealed medication dispensing and administering device as claimed in claim 7, wherein
the first connecting unit has two bayonet hooks disposed at a bottom end of the outer barrel, formed on an inner surface of the outer barrel, and facing to each other; and
the second connecting unit has two buckling recesses laterally defined in the connecting cover; and positions of the two buckling recesses respectively correspond to positions of the two bayonet hooks;
wherein, when the outer barrel is connected to the connecting holder, the two bayonet hooks respectively engage with the two buckling recesses.

10. The sealed medication dispensing and administering device as claimed in claim 7, wherein
the first connecting unit has two engaging hooks disposed at a bottom of the outer barrel and formed on two opposite lateral sides of the outer barrel; each engaging hook has a hook portion and a pressed portion; the hook portion is disposed below the pressed portion and is capable of moving with movement of the pressed portion; and
the second connecting unit has two rods formed at a top end of the connecting holder, and each rod has a top end being hook-like;
wherein, when the outer barrel is connected to the connecting holder, the two hook portions respectively hook the two top ends of the two rods.

11. A sealed medication dispensing and administering device, characterized in that the sealed medication dispensing and administering device comprises:
a syringe having
an outer barrel having an air inlet tube, a rubber stopper, and a connecting hole; the air inlet tube downward extending from a lower face of the outer barrel; the rubber stopper disposed within the air inlet tube and at a positon adjacent to an opening that is at a bottom end of the air inlet tube; the rubber stopper having a slit that is normally closed; and the connecting hole defined through the lower face of the outer barrel and being spaced from the air inlet tube;
an inner barrel inserted inside the outer barrel and having a vent, a medication inlet tube, and a rubber stopper; the vent disposed on an inner surface of the inner barrel and communicating with an inner space of the inner barrel and an inner space of the outer barrel; the medication inlet tube disposed on a lower face of the inner barrel and mounted through the connecting hole of the outer barrel; and the rubber stopper disposed within the medication inlet tube and disposed at a position adjacent to an opening that is at a bottom end of the medication inlet tube; the rubber stopper having a slit that is normally closed; and
a plunger inserted within the outer barrel and the inner barrel and being moveable up and down, the plunger having a piston at a bottom end of the plunger, and the piston longitudinally dividing the inner space of the inner barrel into two parts that are free from communicating with each other;
a connecting holder detachably connected to the syringe and having
a connecting cover having at least one outer connecting hole; and
two piercing needles disposed within the connecting cover and respectively having two tips facing upward, and the two piercing needles respectively and selectively piercing through the slit of the rubber stopper disposed within the medication inlet tube and the slit of the rubber stopper disposed within the air inlet tube; each piercing needle having an inner space being independent from each other and a first opening, the inner space of each piercing needle communicating with the at least one outer connecting hole of the connecting cover, and the first opening disposed at the tip of the piercing needle;
an elastic valve made of a flexible material that is compressible, the elastic valve disposed within the connecting cover; the elastic valve selectively covering the two piercing needles; the elastic valve having two notches; the two notches respectively disposed above the two piercing needles, and the two notches normally being open and respectively and selectively pierced through by the two piercing needles; and
a check valve disposed within the connecting cover; a position of the check valve corresponding to a position of the inner space of one of the two piercing needles that corresponds to the air inlet tube in position; and the check valve making air flow uni-directionally through the check valve.

12. The sealed medication dispensing and administering device as claimed in claim 11, wherein the connecting holder further has a penetrating needle and a phial engaging portion; the penetrating needle is disposed at a bottom of the connecting holder; the penetrating needle is connected to the connecting cover; an inner space of the penetrating needle communicates with the inner spaces of the two piercing needles; the at least one outer connecting hole extends through the penetrating needle; and the phial engaging portion is connected to a bottom of the connecting cover.

13. The sealed medication dispensing and administering device as claimed in claim 11, wherein the connecting holder further has a connecting ring; the connecting ring downward extends from a bottom face of the connecting cover and has an inner thread formed on an inner surface of the connecting ring.

14. The sealed medication dispensing and administering device as claimed in claim 11, wherein the connecting holder further has a Y connector with three ends; one of the three ends of the Y connector is formed on a bottom face of the connecting cover and an inside of the Y connector communicates with the at least one outer connecting hole.

15. The sealed medication dispensing and administering device as claimed in claim 11, wherein the connecting holder further has an intravenous administration set; the intravenous administration set has an adaptor and a spike; a lateral wall of the adaptor is connected to a bottom of the connecting cover, and an inside of the adaptor communicates with the at least one outer connecting hole; and the spike is disposed at an end of the adaptor.

* * * * *